United States Patent
Liu et al.

(10) Patent No.: US 9,606,056 B2
(45) Date of Patent: Mar. 28, 2017

(54) SELECTION OF SPECTRAL BANDS OR FILTERS FOR MATERIAL CLASSIFICATION UNDER MULTIPLEXED ILLUMINATION

(71) Applicant: CANON KABUSHIKI KAISHA, Tokyo (JP)

(72) Inventors: Chao Liu, Irvine, CA (US); Sandra Skaff, Mountain View, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 224 days.

(21) Appl. No.: 14/309,771

(22) Filed: Jun. 19, 2014

(65) Prior Publication Data

US 2015/0160128 A1    Jun. 11, 2015

Related U.S. Application Data

(60) Provisional application No. 61/913,074, filed on Dec. 6, 2013.

(51) Int. Cl.
*G01N 21/55* (2014.01)
*G06N 99/00* (2010.01)
(Continued)

(52) U.S. Cl.
CPC ............ *G01N 21/55* (2013.01); *G06K 9/209* (2013.01); *G06K 9/2018* (2013.01); *G06K 9/628* (2013.01);
(Continued)

(58) Field of Classification Search
CPC ... G01B 9/04; G01N 21/4795; G01N 15/1459
(Continued)

(56) References Cited

U.S. PATENT DOCUMENTS 3,747,755 A * 7/1973 Senturia .................. B07C 5/342
  209/559
4,311,393 A   1/1982 Bartke .......................... 356/407
(Continued)

FOREIGN PATENT DOCUMENTS

GB      2119509 A  * 11/1983  ........... B07C 5/3425
WO   2011/014282       2/2011

OTHER PUBLICATIONS

Imai, Francisco, et al., "Comparison of Spectrally Narrow-Band Capture Versus Wide-Band with Priori Sample Analysis for Spectral Reflectance Estimation", 2000, IS&T.
(Continued)

*Primary Examiner* — Kara E Geisel
*Assistant Examiner* — Dominic J Bologna
(74) *Attorney, Agent, or Firm* — Fitzpatrick Cella Harper & Scinto

(57) ABSTRACT

Material classification using multiplexed illumination by broadband spectral light from multiple different incident angles, coupled with multi-spectral narrow band spectral measurement of light reflected from the illuminated object of unknown material, wherein selection of spectral bands for illumination or for narrow-band capture may comprise analysis of a database of labeled training material samples within a multi-class classification framework, captured using a relatively large number of spectral bands (such as 32 spectral bands), so as to select a subset of a relatively fewer number of spectral bands (such as 5 spectral bands), wherein the selected spectral bands in the subset retain a significant aptitude for distinguishing between different classifications of materials.

31 Claims, 11 Drawing Sheets

(51) Int. Cl.
  *G06K 9/20* (2006.01)
  *G06K 9/62* (2006.01)
(52) U.S. Cl.
  CPC ... *G06N 99/005* (2013.01); *G01N 2201/0627* (2013.01); *G01N 2201/129* (2013.01)
(58) Field of Classification Search
  USPC .................. 356/445, 450–456, 337, 336
  See application file for complete search history.

(56) References Cited

U.S. PATENT DOCUMENTS

| | | | |
|---|---|---|---|
| 5,348,002 A | 9/1994 | Caro | 128/633 |
| 5,424,543 A | 6/1995 | Dombrowski et al. | 250/330 |
| 7,929,142 B2 | 4/2011 | Ben-Ezra et al. | 356/445 |
| 8,189,189 B1 | 5/2012 | Herendeen et al. | 356/300 |
| 9,155,475 B2* | 10/2015 | Xu | H04N 5/2256 348/370 |
| 9,417,185 B1* | 8/2016 | Bruce | G06T 15/04 |
| 2006/0245632 A1* | 11/2006 | Nisper | G01J 3/02 382/135 |
| 2009/0213120 A1* | 8/2009 | Nisper | G01J 3/504 345/426 |
| 2010/0080456 A1* | 4/2010 | Paul | B07C 5/3422 382/165 |
| 2010/0290032 A1* | 11/2010 | Bugge | B07C 5/342 356/51 |
| 2011/0243450 A1* | 10/2011 | Liu | G06K 9/00577 382/190 |
| 2011/0261355 A1 | 10/2011 | Hannel et al. | 356/303 |
| 2014/0010443 A1 | 1/2014 | Imai | 382/165 |
| 2015/0015887 A1* | 1/2015 | Tin | G01N 21/55 356/445 |

OTHER PUBLICATIONS

C. Hahlweg and H. Rothe, "Classification of Optical Surface Properties and Material Recognition Using Multi-Spectral BRDF Data Measured With Semi-Hemispherical Spectro-Radiometer in VIS and NIR", SPIE 5965-16, 2005.

Wang, O.; Gunawardane, P.; Scher, S. and Davis, J., "Material classification using BRDF slices", CVPR, 2009.

Gu, J. and Liu, C., "Discriminative Illumination: Per-Pixel Classification of Raw Materials based on Optimal Projections of Spectral BRDF", CVPR, 2012.

Gu, J., et al., "Classifying Raw Materials With Discriminative Illumination", Project Home Page, Rochester Institute of Technology, <http://www.cis.rit.edu/jwgu/research/fisherlight/>, visited Jun. 19, 2013.

Varma, M. and Zisserman, A., "A statistical approach to material classification using image patch exemplars", IEEE PAMI, 2009.

Liu, C.; Sharan, L.; Adelson, E. H. and Rosenholtz, R., "Exploring features in a Bayesian framework for material recognition", IEEE CVPR, 2010.

Hu, D. J.; Bo, L. and Ren, X., "Toward robust material recognition of everyday objects", BMVC, 2011.

U.S. Appl. No. 61/736,130, filed Dec. 12, 2010 by Francisco Imai, entitled "Systems and Methods for Material Classification Based on Decomposition of Spectra into Sensor Capturing and Residual Components".

U.S. Appl. No. 13/887,163, filed May 3, 2013 by Francisco Imai, entitled "Method for Simultaneous Colorimetric and Spectral Material Estimation".

U.S. Appl. No. 14/092,492, filed Nov. 27, 2013 by Sandra Skaff, entitled "Material Classification Using BRDF (Bidirectional Reflectance Distribution Functions) Slices".

* cited by examiner

SELECTION OF SPECTRAL BANDS OR FILTERS FOR MATERIAL CLASSIFICATION UNDER MULTIPLEXED ILLUMINATION

CROSS REFERENCE TO RELATED APPLICATION

This application claims priority from U.S. Provisional Application No. 61/913,074, filed Dec. 6, 2013, the contents of which are incorporated by reference herein as if set forth in full.

FIELD

The present disclosure relates to material classification in which an object fabricated from an unknown material is illuminated with light, and light reflected therefrom is measured in an effort to identify the unknown material.

BACKGROUND

Material classification using texture images has been heavily researched. However, only recently has material classification using BRDFs (Bidirectional Reflectance Distribution Functions) been introduced [1], and consequently using spectral BRDFs [2]. Additionally, a dataset of spectral BRDFs of material samples has been published in 2012 by RIT (http://compimgl.cis.rit.edu/data/metal/). The dataset contains 100 material samples of 10 main categories. The setup for image capture constitutes a dome of 25 clusters, with 6 LEDs in each cluster. The 6 LEDs are of colors blue, green, yellow, red, white, and orange. The spectra of these LEDs are wide-band and are limited in number.

CITATIONS

1. Wang, O.; Gunawardane, P.; Scher, S. and Davis, J., "Material classification using BRDF slices", CVPR, 2009.
2. Gu, J. and Liu, C., "Discriminative Illumination: Per-Pixel Classification of Raw Materials based on Optimal Projections of Spectral BRDF", CVPR, 2012.
3. Gu, J., et al., "Classifying Raw Materials With Discriminative Illumination", Project Home Page, Rochester Institute of Technology, <http://www.cis.rit.edu/jwgu/research/fisherlight/>, visited Jun. 19, 2013.
4. Varma, M. and Zisserman, A., "A statistical approach to material classification using image patch exemplars", IEEE PAMI, 2009.
5. Liu, C.; Sharan, L.; Adelson, E. H. and Rosenholtz, R., "Exploring features in a Bayesian framework for material recognition", IEEE CVPR, 2010.
6. Hu, D. J.; Bo, L. and Ren, X., "Toward robust material recognition of everyday objects", BMVC, 2011.

SUMMARY

There has apparently been only one approach in the literature which uses spectral BRDF-based features and coded illumination to classify materials. See Gu at [2]. The imaging framework consists of an LED-based multispectral dome and the hemispherical geodesic dome has 25 LED clusters. Each LED cluster has 6 color LEDs over the visible wavelength range, the colors of which are blue, green, yellow, red, white, and orange. The same LEDs are used to image all material samples, and they are limited in number to 6.

The previous approach which uses spectral BRDF based features for material classification uses 150 LEDs for capturing the material images. As described in the previous section, the LEDs are the same for all material images, their spectra are broadband, and they are limited in number to six (6).

Described herein is an embodiment which uses 32 narrow spectral bands as compared with 6 broadband ones for imaging materials for the purpose of classifying them. In this embodiment, these 32 bands are obtained through the usage of a Liquid Crystal Tunable Filter (LCTF) mounted in front of the camera lens. FIG. 6 shows the spectral transmissions of the 32 bands as provided by the manufacturer. There are 32 narrow spectral bands in total ranging from 410 nm to 720 nm with an interval of 10 nm. Imaging materials with narrow bands would provide images which are more discriminative in terms of subtle changes in the spectral reflectance of different materials.

Also described herein is an embodiment by which a subset of fewer than the 32 filters is selected. The subset may, for example, contain five (5) filters selected from the 32 filters, and the filters in the subset are selected in such a way as to provide significant discrimination among the materials to be classified. Reducing the number of filters needed, from a first large number such as 32 to a second lower number such as 5, has several advantages in a recycling factory or other industrial inspection or robotic application settings. These advantages include reducing capture time, reducing cost through replacing an expensive LCTF with a filter wheel which would use around 5 filters, and providing the potential to design a color filter array for material sensing. These advantages are described in more detail below.

Aspects described herein thus include selection of spectral bands using spectral BRDF slice images captured under multiplexed illumination for material classification, and may comprise analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials.

According to further aspects described herein, analysis may comprise access to a database of labeled training material samples within a multi-class classification framework, the samples being captured using a relatively large number of spectral bands, computation of feature vector representations of these materials, machine-learning of a set of weights representing the importance of the spectral bands on the features in each binary classification task, conversion of weights from the binary classification tasks to a set of weights for the multi-class classification framework using a mapping function, and selecting spectral bands of highest weight as the selected spectral bands.

According to still further aspects described herein, a set of weights may be learned by application of an Adaboost algorithm. A classification engine may be trained using the selected spectral bands, the corresponding images obtained using them, and feature vector representations computed from the material samples using these images. Material sub-categories may be considered. The feature vectors may be pixel intensities of spectral BRDF slice images captured under multiplexed illumination, and the feature vector representations may be learned using pixel intensities of spectral BRDF slice images captured under multiplexed illumination. The training images may be labeled by material by calculating a probability function based on determining a correlation between a sample signature and a set of pre-labeled signatures in a database. The number of selected spectral bands may be selected automatically, for example, using thresholding on the weights.

Aspects described herein also include selection of spectral bands using spectral BRDF slice images captured under multiplexed illumination for material classification, by accessing a database of labeled training material samples within a multi-class classification framework, captured using a relatively large number of spectral bands; computing feature vector representations of these materials; learning a set of weights representing the importance of the spectral bands, using Adaboost for example, on the features in each binary classification task; converting the weights from the binary classification tasks to a set of weights for the multi-class classification framework using a mapping function; and selecting spectral bands of highest weight as the selected spectral bands. A classification engine may be trained using the selected spectral bands, the corresponding images obtained using them, and feature vector representations computed from the material samples using these images.

According to such aspects, the feature vectors may be pixel intensities of spectral BRDF slice images captured under multiplexed illumination, or the feature vector representations may be learned using pixel intensities of spectral BRDF slice images captured under multiplexed illumination. The training images may be labeled by material by calculating a probability function based on determining a correlation between a sample signature and a set of pre-labeled signatures in a database. The number of selected spectral bands may be selected automatically, for example, using thresholding on the weights. Material sub-categories may be considered.

With respect to labeling of training images by material by calculating a probability function based on determining a correlation between a sample signature and a set of pre-labeled signatures in a database, reference is made to the following which are incorporated herein by reference as if set forth herein in full: (1) U.S. Provisional Application No. 61/736,130, filed Dec. 12, 2012 and assigned to the Applicant herein, entitled "Systems and Methods for Material Classification Based on Decomposition of Spectra into Sensor Capturing and Residual Components" by Francisco Imai; and (2) U.S. application Ser. No. 13/887,163, filed May 3, 2013 and assigned to the Applicant herein, entitled "Method for Simultaneous Colorimetric and Spectral Material Estimation" by Francisco Imai, now published at U.S. Patent Application Publication No. 2014/0010443.

Aspects described herein also include material classification of an object fabricated from an unknown material, and may comprise illuminating an object by multiplexed illumination such as by using multiple broadband light sources, measuring multiple spectral bands of light reflected from the illuminated object, and classifying the material from which the object is fabricated using the measured reflected light. With respect to the measured multiple spectral bands, wavelengths for the multiple spectral bands may be selected by analysis of a database of labeled training material samples within a multi-class classification framework, captured using a relatively large number of spectral bands, so as to select a subset of a relatively fewer number of spectral bands, wherein the selected spectral bands in the subset have a significant aptitude for distinguishing between different classifications of materials in the database.

With respect to the spectral bands at which light reflected from the illuminated object is measured, the spectral bands may be implemented as spectral bands from a spectrally-narrow light source or sources, or as spectral filters on the light source or on the reflected light, or as combinations thereof.

According to aspects described herein, the multiple spectral bands may be selected by steps which include computing feature vector representations of the materials in the database, learning a set of weights representing the importance of the spectral bands, using Adaboost for example, on the features in each binary classification task, converting the weights from the binary classification tasks to a set of weights for the multi-class classification framework using a mapping function, and selecting spectral bands of highest weight as the selected spectral bands.

Further according to such aspects, feature vector representations may be computed from the measured spectral bands. The feature vectors may be pixel intensities of spectral BRDF slice images captured under multiplexed illumination, or the feature vector representations may be learned using pixel intensities of spectral BRDF slice images captured under multiplexed illumination.

Further according to such aspects, classification may comprise applying a trained classification engine to the captured light information to classify the material of the illuminated object. Material sub-categories may be considered. The trained classification engine may make a decision for cases with a pre-determined level of confidence in the prediction. When a decision is not made, the sample may be subjected to manual labeling. The trained classification engine may be trained on-line with new material samples. The trained classification engine may make a decision for cases with a pre-determined level of confidence in the prediction, wherein when a decision is not made, the sample is subjected to manual labeling in which the sample is placed into an online material classifier.

According to further aspects, the disclosure herein describes finding a subset of spectral bands that are optimized to classify the materials in a group of materials. The optimized subset of spectral bands allows classification of the materials in the group of materials without a significant loss of classification accuracy. Thus, given a set of materials, a set of spectral bands, and a first group of materials that are to be classified, the system determines a subset of spectral bands that is optimized to detect the first group. Different optimized subsets of spectral bands may be generated for the different groups of materials. For example, even though two groups of materials might overlap, their respective optimized subsets of spectral bands do not necessarily overlap. Also, although two groups of materials might not overlap, their respective optimized subsets of spectral bands might in fact overlap.

This brief summary has been provided so that the nature of this disclosure may be understood quickly. A more complete understanding can be obtained by reference to the following detailed description and to the attached drawings.

BRIEF DESCRIPTION OF THE DRAWINGS

FIGS. 4 and 5 illustrate a further embodiment for the determination and calculation of the spectral wavebands used by the classification system depicted in FIG. 1, wherein FIG. 4 illustrates an embodiment in which a training sample of objects fabricated from known materials is subjected to illumination from multiple light sources, and wherein FIG. 5 illustrates more details concerning the internal architecture of a light source configuration controller and analyzer.

DETAILED DESCRIPTION

<Architecture>

Figure 1:
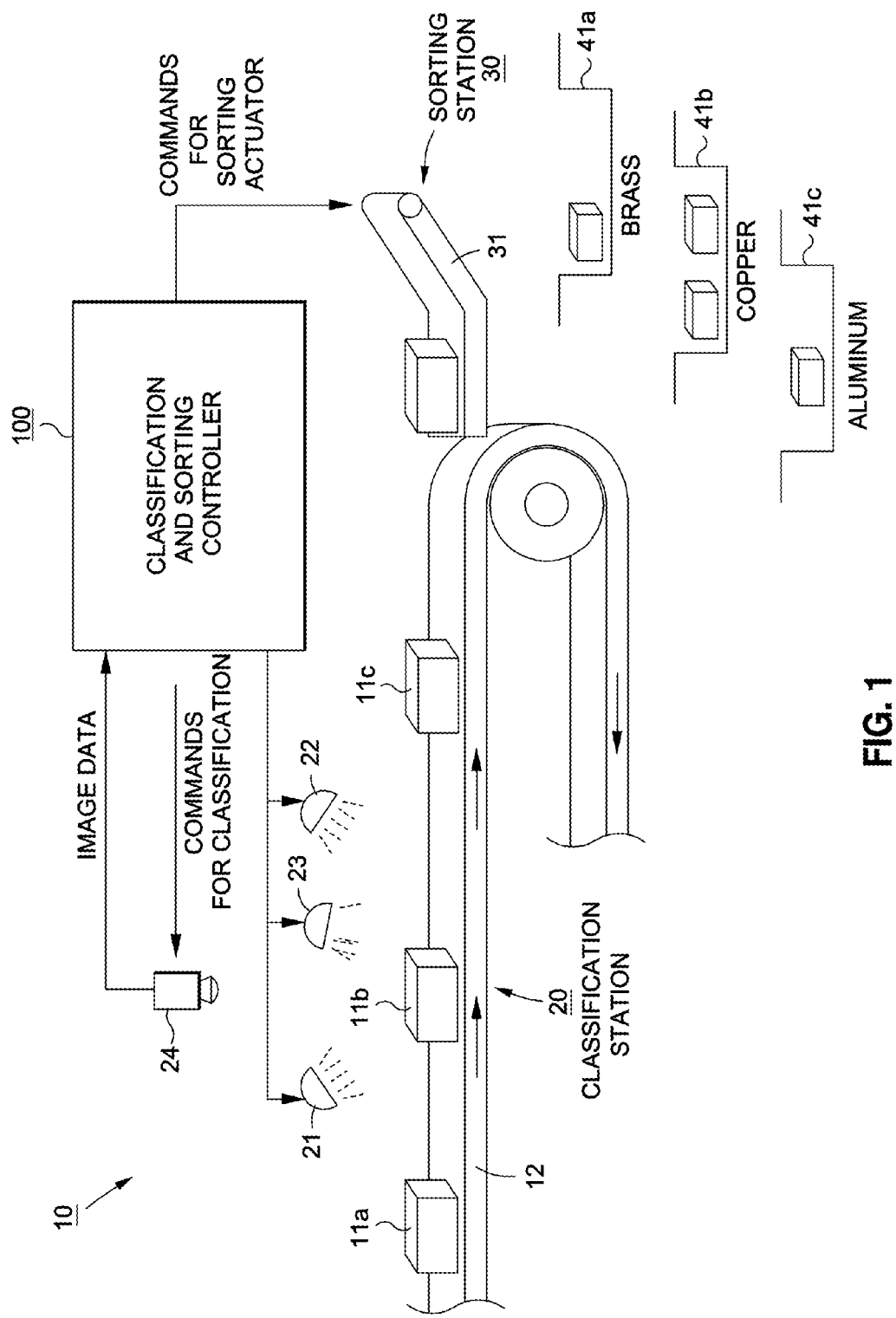
FIG. 1 is an example embodiment of a classification system according to the description herein, in the form of a robotic industrial inspection system.

FIG. 1 is an example embodiment of a classification system according to the description herein, in the form of an industrial inspection system such as a recycling system in which objects to be recycled are classified according to the materials from which the objects are fabricated, and the classified objects are sorted for recycling according to their material classification.

As shown in FIG. 1, objects 11a, 11b, etc. are conveyed on a conveyor mechanism 12 to a classification station 20, where the objects are classified according to their material, and thence to a sorting station 30, where the objects are sorted according to their material classification. Classification station 20 includes plural broadband light sources 21, 22 and 23, together with a camera 24 for capturing images of objects positioned at classification station 20. The object at the classification station is illuminated by multiplexed illumination by simultaneously using all of the plural broadband light sources under control of classification and sorting controller 100, and camera 24 captures one or more images for each multiplexed illumination. Under control of the classification and sorting controller 100, a classification is made for the material from which the object is fabricated.

Camera 24 is a multi-spectral capture camera, capable of capturing images in each of plural spectral bands which are narrow, such as in each of 32 spectral bands ranging from 410 nm to 720 nm with an interval of 10 nm. For example, camera 24 may be a broad-band capture camera with a tunable filter positioned before it, such as a liquid crystal tunable filter (LCTF) with 32 spectral bands ranging from 410 nm to 720 nm with an interval of 10 nm.

More preferably, however, while being a multi-spectral capture camera, capable of capturing images in each of plural spectral bands which are narrow, camera 24 does not necessarily have the capability of capturing images in all 32 spectral bands ranging from 410 nm to 720 nm with an interval of 10 nm. Rather, camera 24 more preferably is equipped to capture images in a subset of fewer than the 32 of spectral bands, such as a subset of 5 spectral bands. The precise identity of the spectral bands selected for the subset, and methodology by which the selection is effected, are both described in greater detail below, in connection with FIGS. 4 through 13.

Because camera 24 preferably captures images in only a subset of spectral bands (such as 5 spectral bands), the camera may be a relatively inexpensive camera since it is not necessary to capture all 32 spectral bands. As an example, the camera 24 may be implemented with a simple filter wheel in front of the camera, or in front of a light source which may be a broadband light source, with filters on the filter wheel corresponding in wavelength to the spectral bands selected for the subset.

Conveyor mechanism 12 continues to convey the object to sorting station 30, where sorting actuator 31 sorts the objects according to the material classification. Sorting is controlled by classification and sorting controller 100, which commands actuator mechanism 31 to sort the classified objects into multiple receptacles 41a, 41b and 41b.

In this example embodiment, material classification differentiates between different types of metals from which the objects are fabricated, such as brass, copper and aluminum. Naturally, it will be understood that this is a non-limiting example. In other embodiments, material classification could differentiate between metal, plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

A description will now be made of the spectral content of the light sources, of the angular positioning of the plural light sources and the camera relative to the object at the classification station, and of the spectral sensitivity of the camera.

Figure 2:
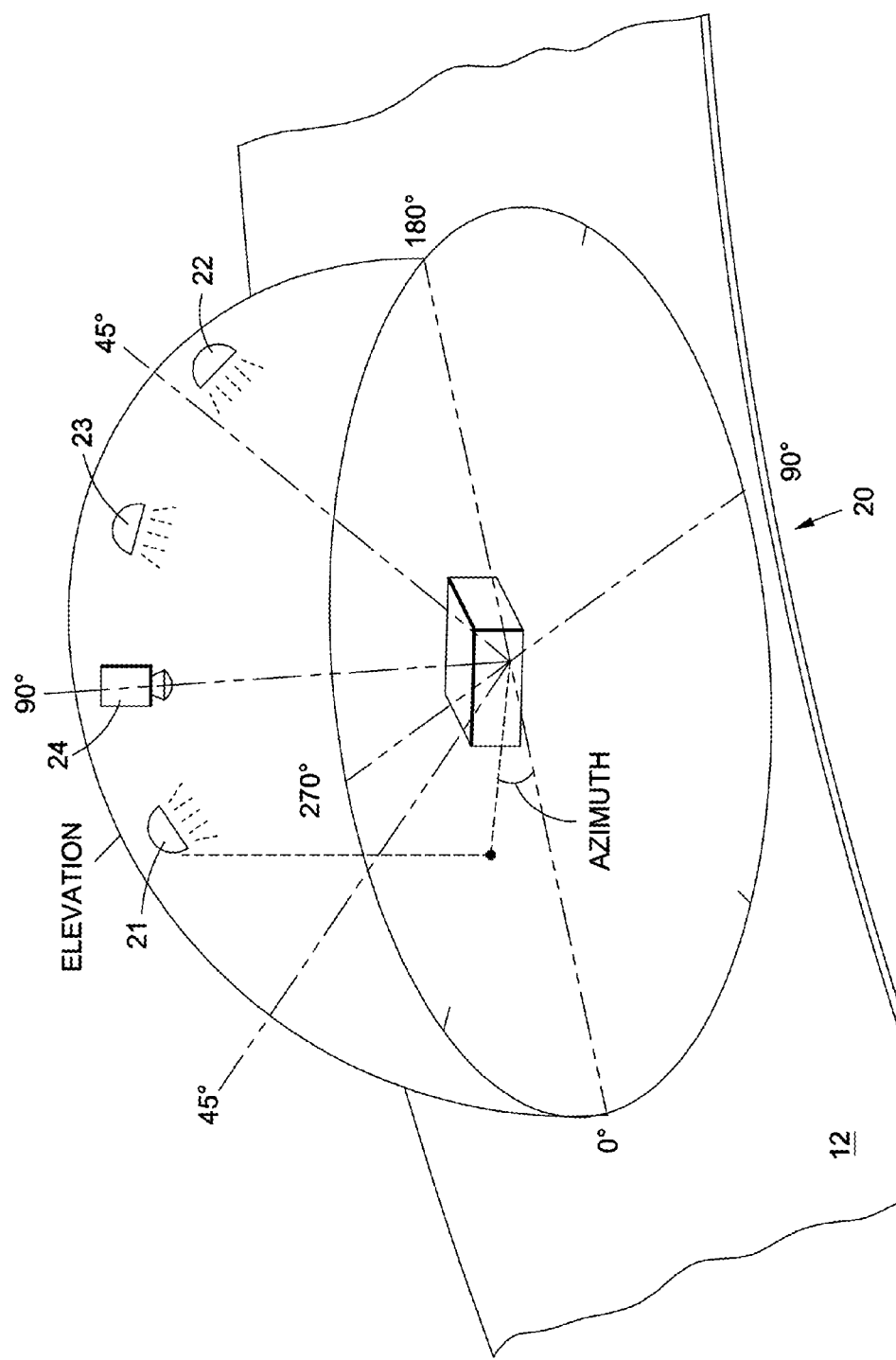
FIG. 2 is a more detailed view of an object on the conveyor mechanism of FIG. 1.

FIG. 2 is a more detailed view of an object being subjected to classification at a classification station of the FIG. 1 view. In FIG. 2, an object is positioned on conveyor mechanism 12 at classification station 20. Each of the light sources 21, 22 and 23 has a broadband spectral content so as to provide multiplexed illumination of the object at classification station 20. In multiplexed illumination, multiple light sources illuminate the object simultaneously from different directions.

In FIG. 2, an angular coordinate system has been superimposed for purposes of explanation, and for purposes of explaining the angle of incidence for each of light sources 21, 22 and 23, and the angle of exitant for light reflected from the object and imaged by camera 24. For purposes of illustration, the elevational and azimuthal angles of only one light source has been depicted, namely, the elevational and azimuthal angles of light source 21, but it is to be understood that each of the light sources is positioned at respective elevational and azimuthal angles relative to the angular coordinate system. The light sources 21, 22 and 23 may be positioned at incidence angles selected by any means that also provides discriminative illumination for the object under inspection using only a relatively few illumination light sources, such as only 2 to 5 light sources, so as to facilitate distinguishing between different classifications of materials. At present, one preferred means for selecting incidence angles is described in U.S. application Ser. No. 14/092,492, filed Nov. 27, 2013 and assigned to the Applicant herein, entitled "Material Classification Using Spectral BRDF (Bidirectional Reflectance Distribution Functions)

Slices" by Sandra Skaff. The aforementioned U.S. application Ser. No. 14/092,492 is incorporated herein by reference, as if set forth fully herein.

In this example, camera 24 is positioned at an exitant angle of 90 degrees elevation, but this is merely convenient and is not necessarily a limiting feature. The derivation and calculation for this exitant angles is also described in greater detail below in the aforementioned U.S. application Ser. No. 14/092,492.

Camera 24 may be a broadband capture camera which exhibits broad spectral sensitivity across the visible and near-visible ranges of wavelengths, together with a liquid crystal tunable filter (LCTF) positioned in front of the camera so as to provide for multi-spectral image capture with 32 spectral bands ranging from 410 nm to 720 nm with an interval of 10 nm. More preferably, however, and as mentioned above, camera 24 preferably captures images in only a subset of spectral bands (such as 5 spectral bands). Accordingly, in other embodiments contemplated herein, the camera may be a relatively inexpensive camera since it is not necessary to capture all 32 spectral bands. As an example, the camera 24 may be implemented with a simple filter wheel in front of the camera, or in front of a light source which may be a broadband light source, with filters on the filter wheel corresponding in wavelength to the spectral bands selected for the subset As shown in FIG. 2, this example embodiment includes three (3) light sources and one (1) camera. One way to determine the number of light sources, and one way to determine the incident angles of the light sources, is discussed in greater detail in the aforementioned U.S. application Ser. No. 14/092,492. Likewise, the number of cameras, together with their exitant angles, is discussed in greater detail in connection with the same application. In general, however, in order to facilitate rapid classification of materials, such as real-time classification of materials, the number of light sources, and the number of cameras is relatively small, such that materials can be classified with only a single multiplexed illumination. Preferably, the number of light sources should range between two and five, inclusive, most preferably two or three light sources, and the number of cameras should range between one and two, inclusive, most preferably one camera.

Although in this embodiment the spectral content of each individual light source is broadband and is identical to all others, it should be understood that the spectral content of the light sources might differ from each other. Likewise, in embodiments where there are plural cameras, although the spectral sensitivities of the cameras might match, it is also possible for the spectral sensitivities to differ.

Under control of classification and sorting controller 100, an object at inspection station 20 is subjected to multiplexed illumination wherein all of plural broadband light sources 21, 22 and 23 are illuminated simultaneously. Under such multiplexed illumination, camera 24 captures a multi-spectral stack of plural images of light reflected from the object at the exitant angle, one image at each of multiple narrow spectral bands. The captured images are collected by classification and sorting controller 100, and are analyzed thereby, such as by deriving one slice of the so-called bidirectional reflectance distribution function (BRDF). The BRDF is a four-dimensional function that depends on incident and exitant angles, and defines how light is reflected from the surface of an object. With a camera positioned at a fixed exitant angle, only a "slice" of the BRDF is obtained.

Based on the BRDF slices, and other analysis which includes application of a feature vector algorithm to extract feature vectors for each image, and feeding of such feature vectors to a trained classification engine, classification and sorting controller 100 obtains a classification of the material from which the illuminated object is fabricated.

Figure 3:
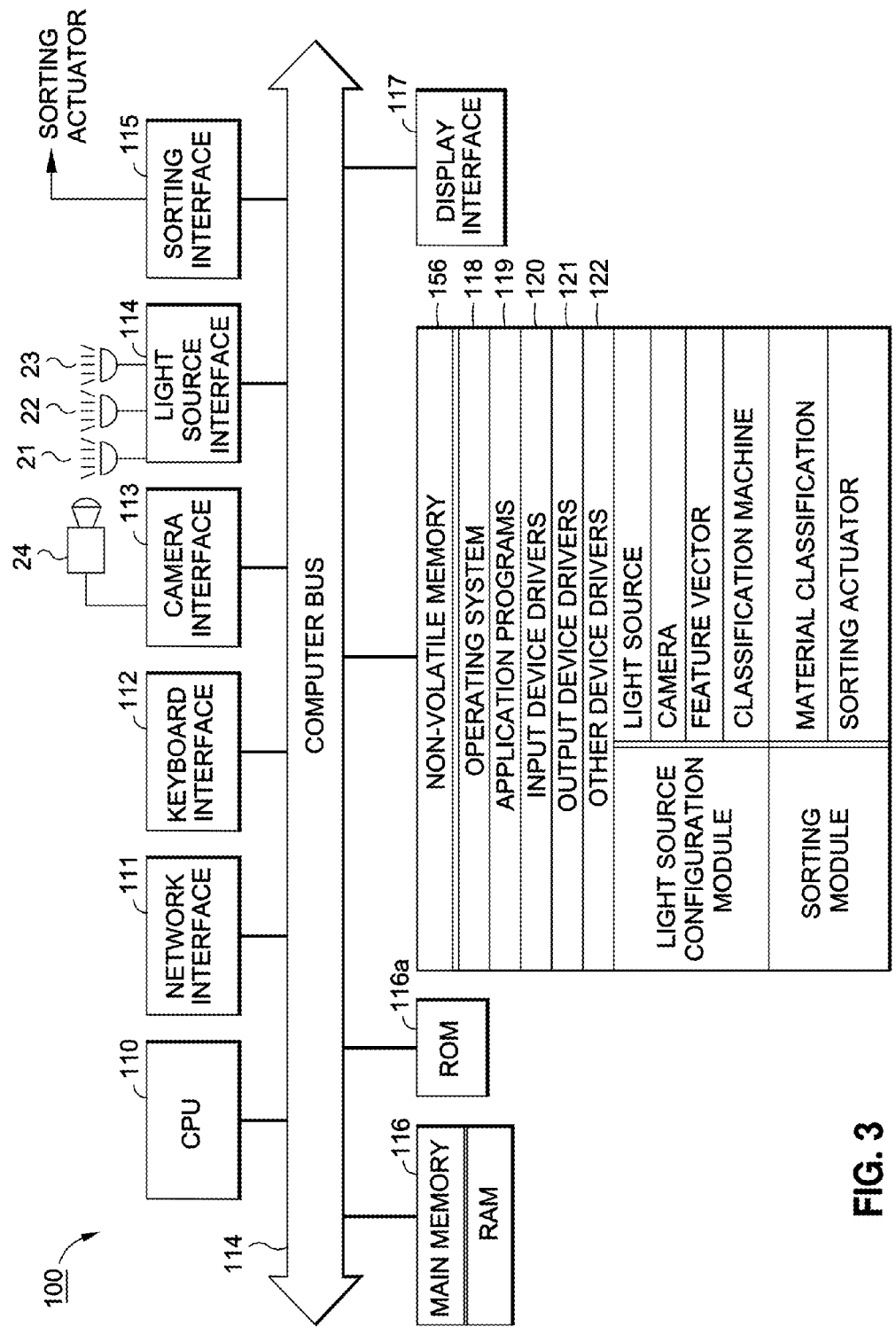
FIG. 3 is a view for explaining the architecture of a classification and sorting controller.

FIG. 3 is a view for explaining the architecture of classification and sorting controller 100.

As shown in FIG. 3, classification and sorting controller 100 includes central processing unit (CPU) 110 which interfaces with computer bus 114. Also interfacing with computer bus 114 are non-volatile memory 156 (e.g., a hard disk or other nonvolatile storage medium), network interface 111, keyboard interface 112, camera interface 113, random access memory (RAM) 116 for use as a main run-time transient memory, read only memory (ROM) 116a, and display interface 117 for a display screen or other output.

RAM 116 interfaces with computer bus 114 so as to provide information stored in RAM 116 to CPU 110 during execution of the instructions in software programs, such as an operating system, application programs, image processing modules, and device drivers. More specifically, CPU 110 first loads computer-executable process steps from non-volatile memory 156, or another non-transitory storage device into a region of RAM 116. CPU 110 can then execute the stored process steps from RAM 116 in order to execute the loaded computer-executable process steps. Data also can be stored in RAM 116 so that the data can be accessed by CPU 110 during the execution of the computer-executable software programs, to the extent that such software programs have a need to access and/or modify the data.

As also shown in FIG. 3, non-volatile memory 156 is an example of non-transitory computer-readable storage medium on which is stored computer-executable process steps for operating system 118, and application programs 119, such as graphic image management programs. Non-volatile memory 156 also stores computer-executable process steps for device drivers for software interface to devices, such as input device drivers 120, output device drivers 121, and other device drivers 122.

Non-volatile memory 156 also stores a material classification module and a sorting module. The material classification module and the sorting module comprise computer-executable process steps for material classification of an object fabricated from an unknown material, and for sorting the object based on the material classification.

The computer-executable process steps for these modules may be configured as part of operating system 118, as part of an output device driver in output device drivers 121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The material classification module includes a corresponding plurality of modules for control of the light sources, for control of the camera(s) and for gathering of image data of such camera(s) a module for derivation of feature vectors according to a feature vector algorithm, such as feature vectors based on BRDF slices, and a classification machine. The classification machine accepts as inputs the feature vectors derived by the feature vector module, and provides a classification of the material from which the object under inspection is fabricated.

The sorting module for its part includes a corresponding plurality of modules related to input of material classification from the classification machine, and actuation of the sorting mechanism based on the classification.

Figure 4:
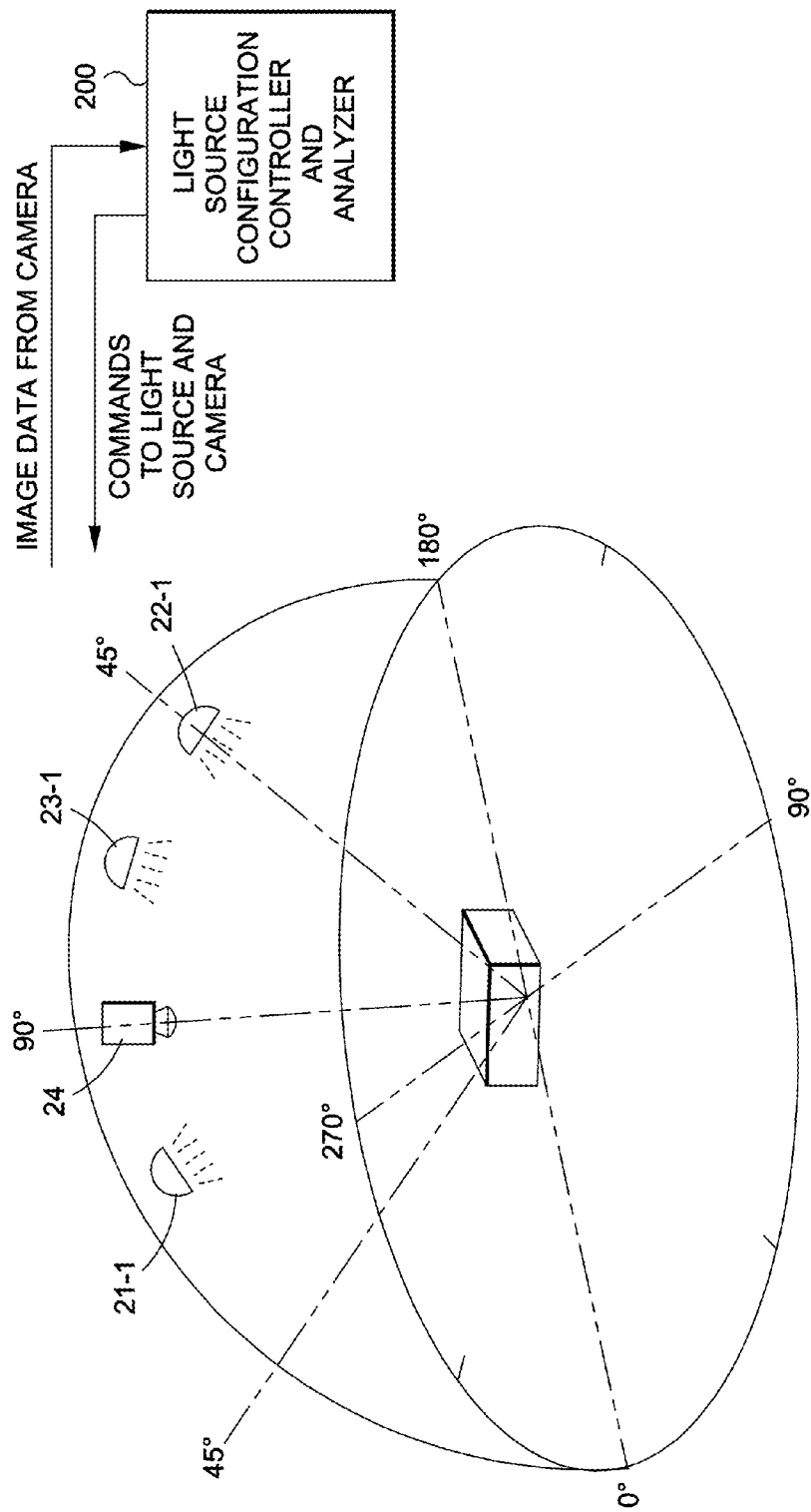
Figure 5:
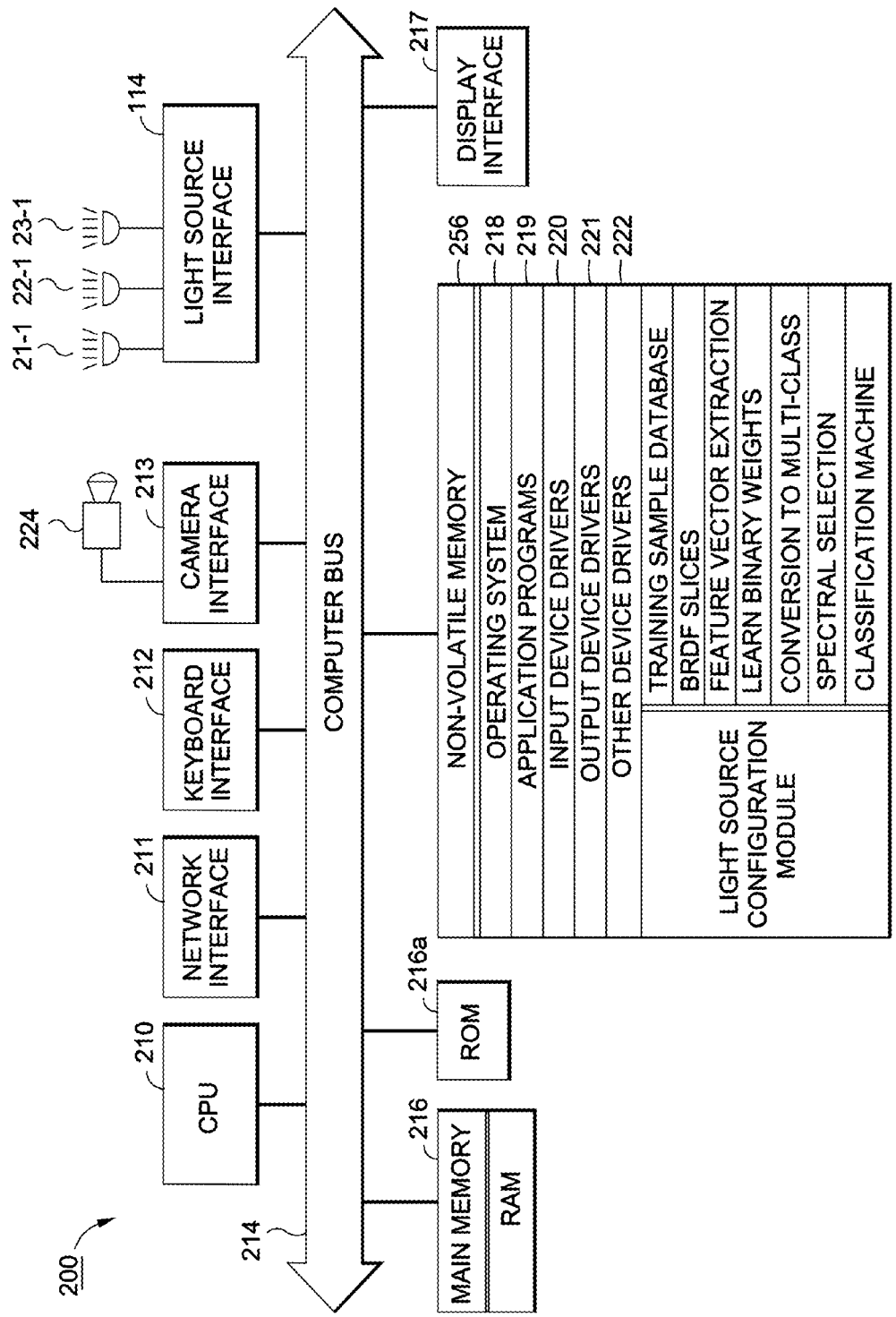

FIGS. 4 and 5 describe a further embodiment according to the description herein. These figures are used to describe the determination and calculation of the spectral wavebands captured by the classification system depicted in FIG. 1.

In particular, FIGS. 4 and 5 describe an embodiment in which a training sample of objects fabricated from known materials is subjected to illumination from plural light sources 21-1, 22-1 and 23-1 of the same number and positioning as the light sources 21, 22 and 23 shown in FIG. 1. One purpose of the arrangement described in FIGS. 4 and 5 is to generate labeled training data over a wide variety of spectral wavebands, and thereafter to use the labeled training data to determine a relatively small subset of spectral wavebands that can be used in the arrangement of FIG. 1 yet still yield effective discrimination and classification of materials.

In one example embodiment, each of light sources 21-1, 22-1 and 23-1 has a broadband spectral content, and each is positioned in azimuth and elevation so as to illuminate the labeled sample from directions that are unlabeled in FIG. 4, for purposes of clarity of illustration.

It should be recognized that more light sources than the three shown in FIGS. 4 and 5 can be used to generate the labeled training data. The training data can be used to determine the position and incidence angles of a subset of light sources having a large discriminative effect on material classification; such a subset thereafter is determinative of the position and incidence angles of the light sources 21, 22 and 23 shown in the industrial inspection system of FIG. 1. For example, twenty-five (25) light sources may be arranged in a hemispherical dome as proposed by Gu in [2]. Labeled training data is generated, and a subset of only a few such light sources is selected, such as three light sources (preferably two to five), together with the training data associated with the light sources in the subset. This process of selecting a small subset of light sources is described in the aforementioned U.S. application Ser. No. 14/092,492.

The labeled training data is used to determine spectral wavebands captured from the multiplexed illumination of the light sources 21, 22 and 23 shown in the industrial inspection system of FIG. 1, with the selected spectral wavebands having a significant aptitude for distinguishing between and classifying materials. A classification machine is trained using the feature vectors corresponding to the spectral wavebands, using the labels from the labeled training sample.

FIG. 4 illustrates an embodiment in which a training sample of objects fabricated from known materials is subjected to illumination from light sources 21-1, 22-1 and 23-1 each with a large broadband spectral content.

In one example embodiment depicted in FIG. 4, there are three light sources, but as explained previously other embodiments might have more, such as twenty-five (25) light sources arranged uniformly over a hemispherical dome surrounding a labeled object in the training sample. One camera 224 is positioned at a predetermined exitant angle such as 90 degrees elevation. Each of the light sources 21-1, 22-1 and 23-1 has a broadband spectral content so as to provide multiplexed illumination of the labeled object in the training sample. In multiplexed illumination, multiple light sources illuminate the object simultaneously from different directions. Camera 224 captures a multi-spectral stack of plural images of light reflected from the object at the exitant angle, one image at each of 32 multiple narrow spectral bands.

Camera 224 is a multi-spectral capture camera, capable of capturing images in each of plural spectral bands which are narrow, such as in each of 32 spectral bands ranging from 410 nm to 720 nm with an interval of 10 nm. For example, camera 224 may be a broad-band capture camera with a tunable filter positioned before it, such as a liquid crystal tunable filter (LCTF) with 32 spectral bands ranging from 410 nm to 720 nm with an interval of 10 nm.

In this embodiment, camera 224 is a broadband capture camera which exhibits broad spectral sensitivity across the visible and near-visible ranges of wavelengths, together with a liquid crystal tunable filter (LCTF) positioned in front of the camera so as to provide for multi-spectral image capture with 32 spectral bands ranging from 410 nm to 720 nm with an interval of 10 nm.

In one preferable arrangement, the spectral content of the light sources in the FIG. 4 embodiment is identical to the spectral content of a corresponding light source in the FIG. 1 classification system. Likewise, the spectral sensitivity of the camera is identical to that of the camera shown in the FIG. 1 classification system. It should be understood, however, that the spectral content of the light sources, and the spectral sensitivity of the camera, might in some embodiments be different.

Operation of the FIG. 4 embodiment proceeds under control of the light source configuration controller and analyzer 200.

FIG. 5 illustrates more details concerning the internal architecture of light source configuration controller and analyzer 200.

As shown in FIG. 5, light source configuration controller and analyzer 200 includes central processing unit (CPU) 210 which interfaces with computer bus 214. Also interfacing with computer bus 214 are non-volatile memory 256 (e.g., a hard disk or other nonvolatile storage medium), network interface 211, keyboard interface 212, camera interface 213, random access memory (RAM) 216 for use as a main run-time transient memory, read only memory (ROM) 216a, and display interface 217 for a display screen or other output.

RAM 216 interfaces with computer bus 214 so as to provide information stored in RAM 216 to CPU 210 during execution of the instructions in software programs, such as an operating system, application programs, image processing modules, and device drivers. More specifically, CPU 210 first loads computer-executable process steps from non-volatile memory 256, or another non-transitory storage device into a region of RAM 216. CPU 210 can then execute the stored process steps from RAM 216 in order to execute the loaded computer-executable process steps. Data also can be stored in RAM 216 so that the data can be accessed by CPU 210 during the execution of the computer-executable software programs, to the extent that such software programs have a need to access and/or modify the data.

As also shown in FIG. 5, non-volatile memory 256 is an example of non-transitory computer-readable storage medium on which is stored computer-executable process steps for operating system 218, and application programs 219, such as graphic image management programs. Non-volatile memory 256 also stores computer-executable process steps for device drivers for software interface to devices, such as input device drivers 220, output device drivers 221, and other device drivers 222.

Non-volatile memory 256 also stores a light source configuration module. The light source configuration module comprises computer-executable process steps for determining, from labeled training data which includes a superset of all spectral content of all light sources, a satisfactory subset of spectral content for light sources by which material classification of an object fabricated from an unknown material may be made accurately and without any significant loss in accuracy as compared to material classification made by the superset.

The computer-executable process steps for these modules may be configured as part of operating system 218, as part of an output device driver in output device drivers 221, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

The light source configuration module includes a corresponding plurality of modules including a module for storing a database of the labeled training sample. The database of labeled training material samples is defined within a multi-class classification framework and is captured using a relatively large number of spectral bands.

The light source configuration module further includes a module for computing feature vector representations of these materials, such as in accordance with application of an algorithm for extraction of feature vectors; a module for learning a set of weights representing the importance of the spectral bands, using Adaboost for example, on the features in each binary classification task; a module for converting the weights from the binary classification tasks to a set of weights for the multi-class classification framework using an appropriate mapping function; and a module for selecting the optimal spectral bands of highest weight as more optimal than other spectral bands for purposes of material classification.

In addition, the light source configuration module further includes a module for storing and training a classification machine. Given the optimal spectral bands as selected above, and given the corresponding images obtained using them, the feature vector representations of the material samples may be computed using these images. Then a classification engine is trained, such as SVM, on the set of features of the training samples. The trained classification engine along with an imaging setup including the optimal spectral bands may then be used in a factory setting such as the industrial inspection system of FIG. 1 to obtain images of and classify new material samples as observed.

<Framework>

Referring again to the architectures described in FIGS. 1 through 5 above, an implementation will now be described.

As described herein, selecting spectral bands for material classification involves image capture and estimation of multiplexed images, applying machine learning techniques such as Adaboost to estimate the weight of each spectral band in a binary classification framework, selecting the spectral bands which provide most discrimination among a set of materials in multi-class classification, and material classification.

With regard to selecting spectral bands or filters for material classification under multiplexed illumination, one motivation is to use 32 narrow spectral bands as compared with 6 broadband ones in the arrangement of Gu at [2] for imaging materials for the purpose of classifying them. In the arrangement of Gu at [2], each light source was composed of a cluster of six differently-colored LEDs, with colors blue, green, yellow red, orange and white, with the white LED positioned at the center of the cluster. In this embodiment, for selecting spectral bands or filters for material classification under multiplexed illumination, five (5) spectral bands are selected from 32 filters which would provide the most discrimination among the materials to be classified.

Figure 6:
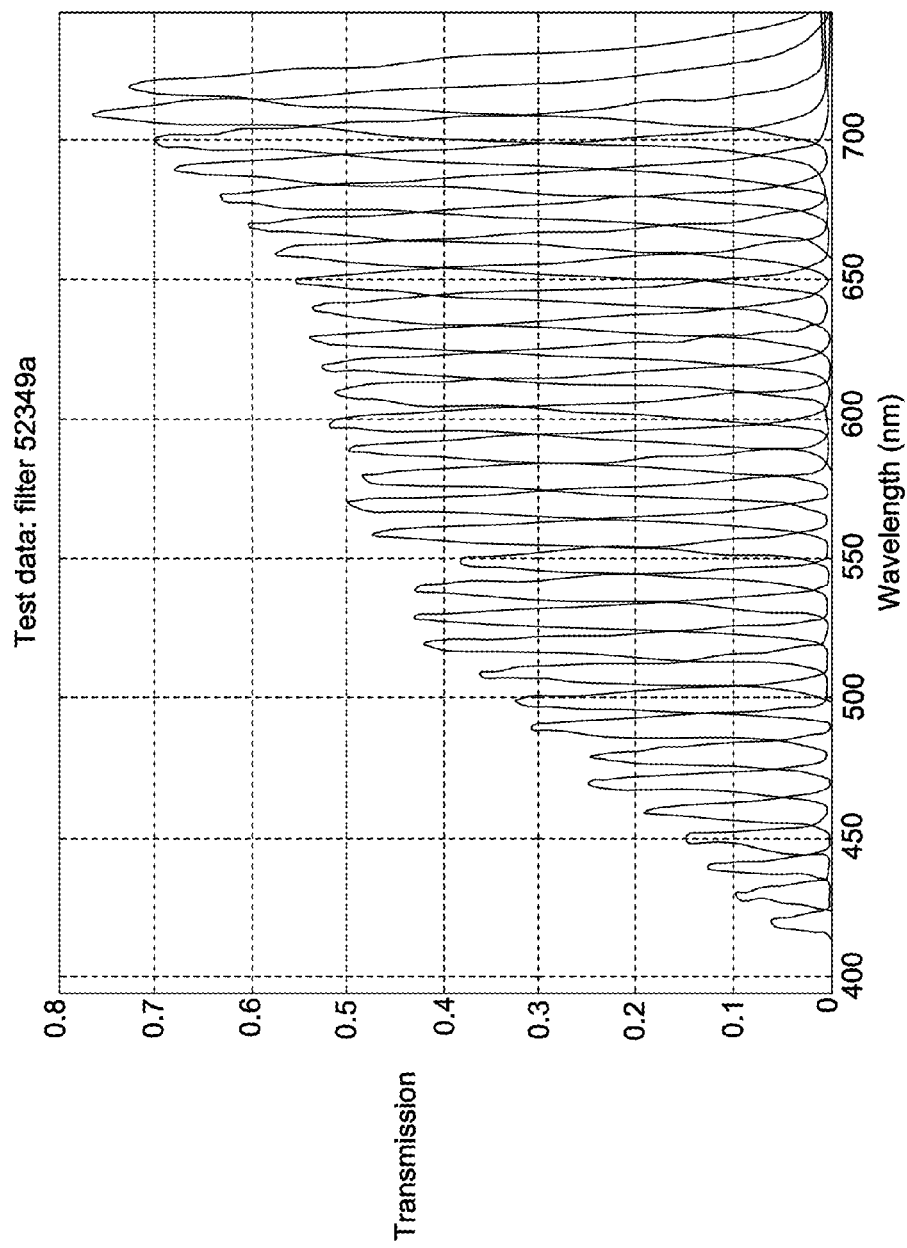
FIG. 6 illustrates transmittance spectra for 32 bands in a LCTF (liquid crystal tunable filter).
Figure 7:
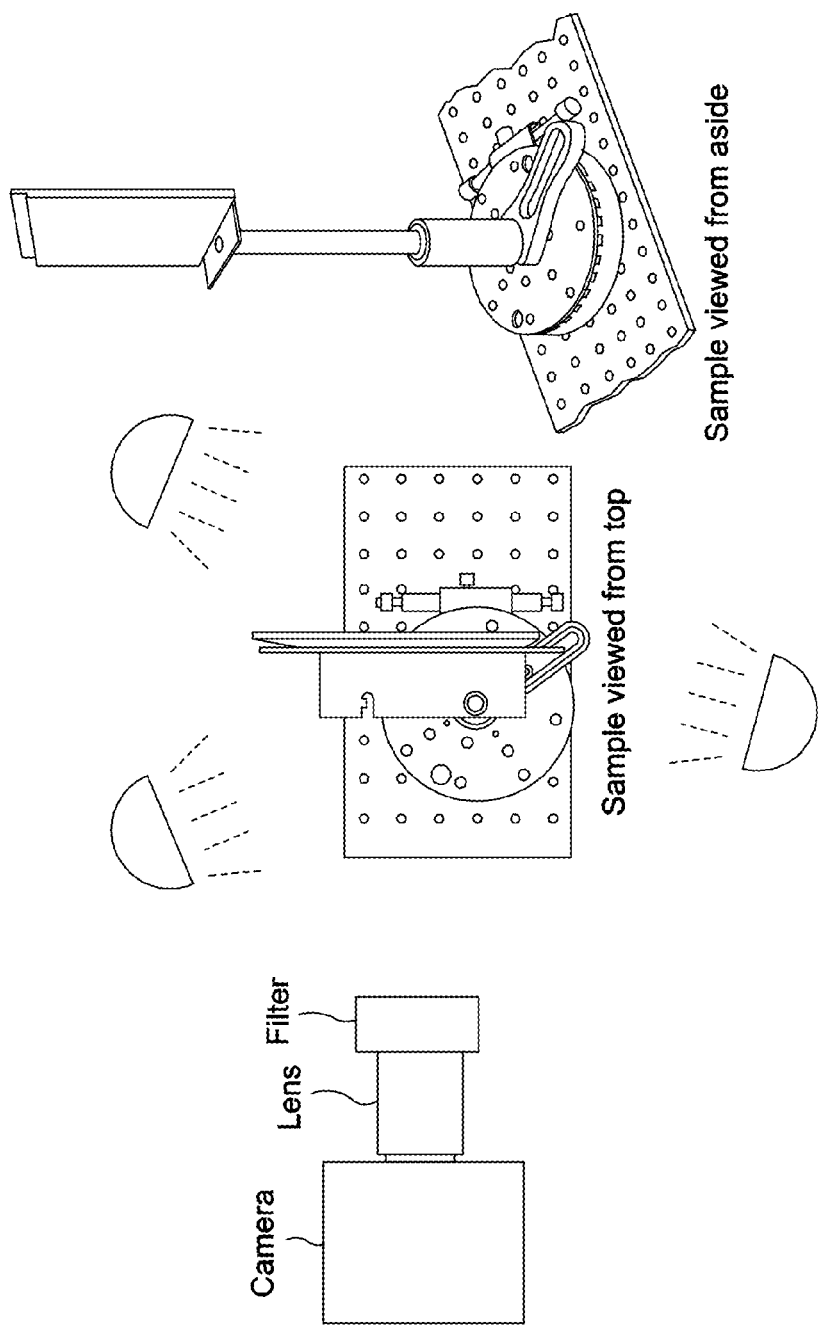
FIG. 7 schematically depicts an image capture configuration.

As for spectral transmittances of the 32 spectral bands in a typical Liquid Crystal Tunable Filter (LCTF), these transmittances are depicted in FIG. 6. In particular, FIG. 6 shows the transmittance spectra for 32 bands in the LCTF FIG. 7 schematically depicts an image capture configuration of this embodiment, in which there are three broadband lights sources that illuminate the sample with broad spectral light, and in which a camera with an LCTF filter positioned in the light path thereof captures multiple different images of the object, each image under a different narrow-band spectral filter as provided by the LCTF filter.

Figure 8:
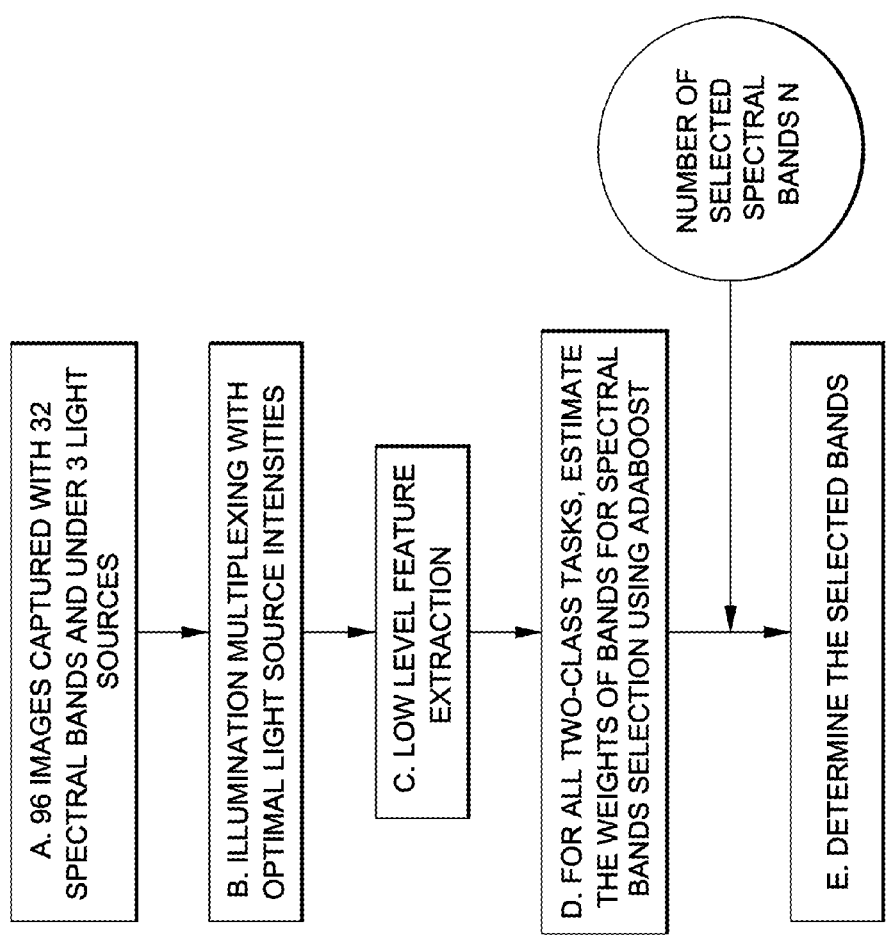
FIG. 8 illustrates a framework for spectral bands selection for material classification under multiplexed illumination.

FIG. 8 shows a framework for the approach described herein. The framework of FIG. 8 includes steps A through E. These steps A through E are described below in Part 1, below, "Steps of the Framework for Selection of Spectral Bands or Filters". In addition, there is a Part 2, also described below, "Training and Classification Using Images Corresponding to the Selected Bands or Filters". Part 2 describes the effect of choosing the optimal subset of filters, such as the compromise on material classification when using images corresponding to a smaller set of filters. Part 2 includes a verification that even the raw measurements or pixel intensities from images corresponding to the optimal spectral bands provide competitive accuracy in material classification.

<Part 1: Steps of the Framework for Selection of Spectral Bands or Filters>

Referring to FIG. 8, the lettered steps A through E therein are explained below.

Step A: Database of Captured Images.

The database of images captured by the FIG. 7 configuration will now be described.

In the database, there were twenty-seven (27) different classes of materials, as follows: Wood (2 different classes), Stainless Steel, ABS plastic-gray, Ceramic, Titanium, HIPS plastic-white, Fabric, Tin, Nitrile rubber-black, Gray Silicone, Aluminum (5 different classes), Copper, Zinc (2 different classes), ABS plastic-white, Brass, Mild Steel, HIPS plastic-white (2 different classes), Steel, Nickel, Lead.

Figure 11:
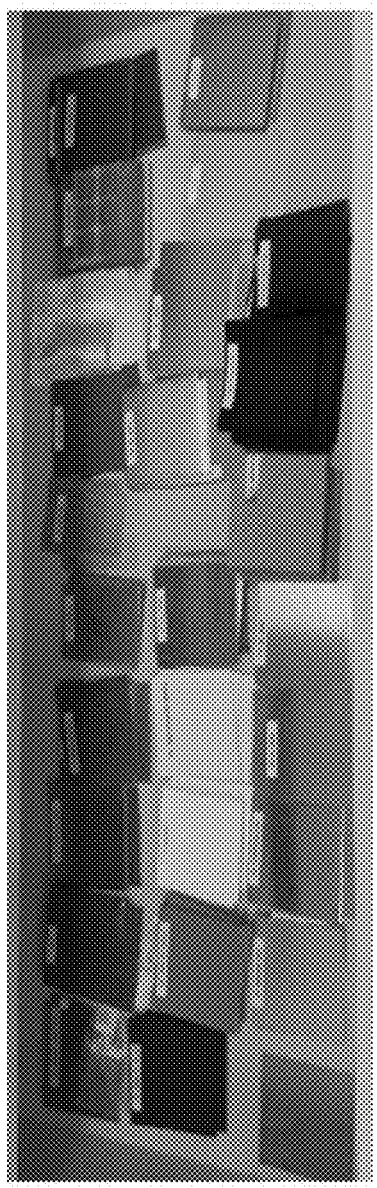
FIG. 11 shows a photograph of twenty-seven (27) classes of material samples used to build a labeled database of training images.

FIG. 11 shows a photograph of the 27 classes of materials used to build the database of one example embodiment As seen in FIG. 11, there are 27 classes, and each class of materials contains 4 samples. Each sample is imaged using 32 spectral narrow bands under 3 directions of incident illumination. As a result, each sample is imaged 96 times with different configurations of spectral bands and illumination directions.

Step B: Illumination Multiplexing.

Given the sets of 3 images captured under different illumination directions in 32 spectral bands, 32 sets of light source intensities for multiplexing are computed so that the multiplexed image for each spectral band is most discriminative. Illumination multiplexing typically consists of capturing the image of the sample under multiple light sources which are illuminated simultaneously to thereby reduce the number of images that need to be captured. However, if there are equipment restrictions, the image may be captured under multiple light sources.

As mentioned, each sample is captured under incident illumination in 3 directions to obtain images $I_1$, $I_2$, and $I_3$. Given the linearity of the image formation process, the multiplexed image is then estimated as a linear combination of images captured when the sample is illuminated by each of the light sources:

$$I = w_1 I_1 + w_2 I_2 + w_3 I_3 \qquad \text{(Equation 1-1)}$$

where the weights w1, w2 and w3 form a vector of weights $\vec{w}$ of light intensities.

One advantage of using illumination multiplexing is increasing the Signal-to-Noise-Ratio (SNR) of the image. This embodiment uses the SVM (Support Vector Machine) with a linear kernel to estimate the light source intensities $\vec{w}$, which are used for estimating the multiplexed image. Other algorithms for discriminative analysis, such as LDA (Linear Discriminant Analysis), can also be used to compute the intensities, although it is preferable that such algorithms are linear.

Table A, below, shows a numerical example of the multiplexed illumination of Step B in the FIG. 8 framework. In the example of Table A, there are three light sources and 32 spectral bands. Each light source is turned on independently, and an image is captured for each one of 32 spectral bands, at full intensity each spectral band. This yields a total of 3×32 image captures, each one at full intensity for one spectral band and at zero intensity for the remaining 31 spectral bands. In this example, intensity is controllable with an 8-bit command, such that intensity is represented as a number between 0 and 255 inclusive. Linearized weighting is applied so that the multiplexed image for each spectral band is most discriminative, thereby to form a vector of weights $\vec{w}$ of light intensities. Table A gives numerical examples of the resulting vector of weights $\vec{w}$ of light intensities w1, w2 and w3. As seen in Table A, each of the weights falls between 0 and 255 inclusive.

TABLE A

|  | band 1 (λ1) | band 2 (λ2) | band 3 (λ3) | band 4 (λ4) | band 5 (λ5) | ... | band 32 (λ32) |
|---|---|---|---|---|---|---|---|
| Weight w1 for Source 1 | 10 | 50 | 30 | 150 | 50 | ... | 100 |
| Weight w2 for Source 2 | 100 | 22 | 12 | 22 | 112 | ... | 94 |
| Weight w3 for Source 3 | 35 | 125 | 50 | 12 | 125 | ... | 40 |

Description of Table A: An example of light source intensities for illumination multiplexing in different spectral bands.

Samples of objects for classification are thereafter illuminated by multiplexed illumination in which all three light sources are turned on simultaneously, and with intensity of each of the 32 spectral bands controlled in accordance with weight vector $\vec{w}$ of light intensities w1, w2 and w3.

Step C: Low-Level Feature Extraction.

Given the multiplexed spectral images, the low-level features are extracted. In this embodiment, the low level features are the concatenations of the pixel values in the images corresponding to the 32 spectral bands. More specifically, each point on the material is considered as a sample point so the low level feature for one point is a 32×1 column vector. Statistics other than the raw pixel values could be used for the features as well, such as the means of pixel values clusters which can be estimated with the K-Means algorithm.

Step D: Weight Estimation.

With the labeled samples and low-level features of samples under multiplexed illumination, the weight indicating the discriminative ability of each spectral band is estimated. Estimation may be made using a classification engine such as a classification engine built by application of the Adaboost algorithm. The Adaboost algorithm takes in the feature in each spectral band as the input for each weak learner, which is a classifier that performs slightly better than random. Then the final inference result is the ensemble of the inferences of all the weak learners. One advantage of using Adaboost for combining the ensemble of weak learners is that it estimates the weights of the weak learners. Because each weak learner corresponds to a specific spectral band, the estimated weights indicate the discriminative abilities of the spectral bands. The spectral band selection is based on those discriminative abilities (i.e. weights). This step is performed for all of the two-class material classification tasks.

Figure 9:
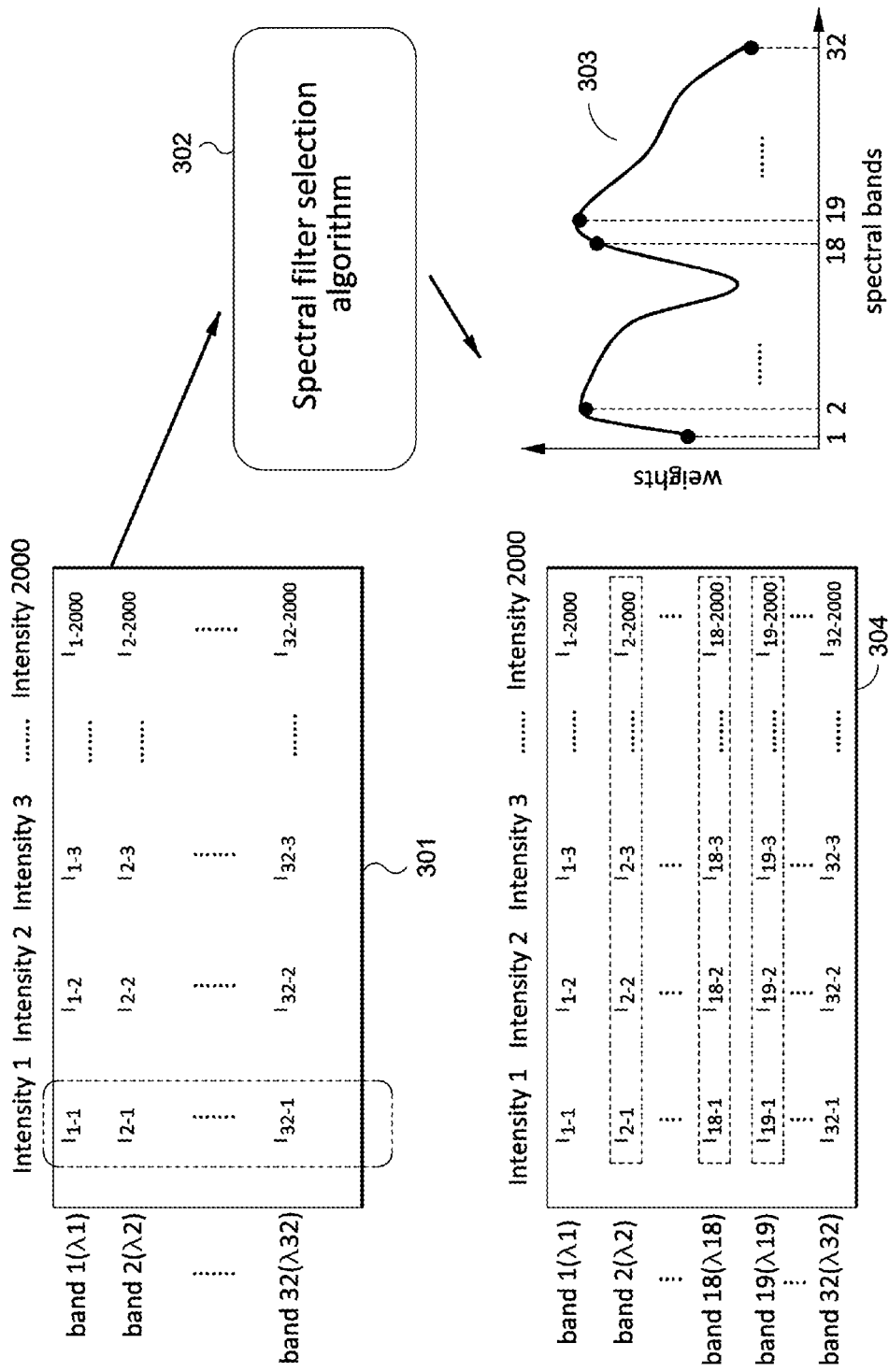
FIG. 9 illustrates selection of weights and spectral bands using the framework of FIG. 8.

FIG. 9 diagrammatically illustrates selection of weights according to Steps C and D of the framework depicted in FIG. 8. FIG. 9 also illustrates selection of spectral bands according to Step E of the framework, and this aspect of FIG. 9 is discussed later. In FIG. 9, reference number 301 refers to the low-level features extracted at Step C. Reference number 302 refers to the weight estimation of Step D, wherein 303 refers to weight determinations for each of the spectral bands, showing spectral bands with the largest weights, and wherein 304 is a repetition of 301 but with highlighting for the spectral bands with the largest weights.

More specifically, reference number 301 is an example of extracted low-level features in the form of acquired intensity values. Intensity 1, highlighted with a dashed line, is a 32×1 column vector including intensity values of each of 32 spectral bands λ1 through λ32 acquired from a first point in a captured image. For example, when the captured image is a rectangle of 40 pixels times 50 pixels, 2000 such column vectors are acquired. All of the column vectors are used as the input of the spectral filter selection algorithm, which is Adaboost in this example embodiment.

Based on the inputted features, the filter selection algorithm depicted at 302 provides two outputs: weight determinations as depicted at 303, and selected spectral bands having the largest weights as depicted at 304. In more detail, filter selection at 302 estimates the weights of all the spectral bands, and provides a determination of weights at each spectral band, as depicted at 303. For purposes of illustration, FIG. 9 shows only five (5) representative weights, at spectral bands corresponding to wavelengths λ1, λ2, λ18, λ19 and λ32. It should be understood, however, that filter selection at 302 estimates weights at all 32 spectral bands.

Reverting to the example embodiment described herein, and with respect to all of the two-class material classification tasks, the classification problem addressed by these experiments may be formulated as follows: Consider a five-class material classification problem: Nickel, Titanium, Tin, Aluminum and Copper. The formulation of the classification problem may therefore be broken down into 10 binary classification problems/tasks, as follows: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

Spectral band selection for the classification problem as so formulated leads to the following Table B, which shows the indexes of the first 5 filters with the largest weights for each of the above ten (10) sets of binary classification tasks within the five-class material classification framework. The last column shows the indexes of the filters selected for the five-class classification framework.

TABLE B

| | Task 1 | Task 2 | Task 3 | Task 4 | Task 5 | Task 6 | Task 7 | Task 8 | Task 9 | Task 10 | All |
|---|---|---|---|---|---|---|---|---|---|---|---|
| Index | 16 | 19 | 5 | 3 | 30 | 16 | 16 | 16 | 16 | 5 | 16 |
| of | 19 | 16 | 30 | 6 | 31 | 19 | 17 | 19 | 19 | 3 | 19 |
| selected | 17 | 18 | 10 | 5 | 14 | 11 | 18 | 9 | 14 | 4 | 5 |
| bands | 28 | 32 | 4 | 32 | 4 | 9 | 32 | 5 | 4 | 30 | 30 |
| | 29 | 21 | 31 | 4 | 18 | 18 | 21 | 3 | 18 | 31 | 3 |

Description of Table B: Indexes of the first 5 filters with the largest weights for each often (10) sets of binary classification tasks within the five-class material classification framework. The materials are Nickel, Titanium, Tin, Aluminum and Copper. In each column, the indexes of filters are arranged in descending order of their weights. The last column shows the set of selected filters after combing the weights. The 10 binary classification tasks correspond to the 10 possible combinations of two materials selected from the five materials of Nickel, Titanium, Tin, Aluminum and Copper. The corresponding task numbers are: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

For each task, there was an estimation of the discriminative ability of each spectral band. The pixels of the material images are taken to be the samples. The low-level features are 32-dimensional. The Adaboost algorithm was used to estimate a weighting coefficient α corresponding to each spectral band by minimizing an exponential loss. Each weak learner corresponds to one spectral band.

The application of the Adaboost algorithm to spectral band selection will now be explained. The given is the training set $(x_1,y_1), \ldots, (x_m,y_m)$ where $x_i$ and $y_i$ are the training data and labels respectively. From this given, the applied Adaboost algorithm is as follows:

For $i = 1, \ldots, m: D_1(i) = 1/m$     (Equation 2-1)

For $t = 1, \ldots, T: h_t = \underset{h_t \in H}{\mathrm{argmax}} |0.5 - \varepsilon_t|,$ where:

$$\varepsilon_t = \sum_{i=1}^{m} D_t(i) I(y_i \neq h_t(x_i))$$ (Equation 2-2)

and I is the indicator function.

$$\alpha_t = \frac{1}{2} \ln \frac{1 - \varepsilon_t}{\varepsilon_t}$$ (Equation 2-3)

Update: $D_{t+1}(i) = \dfrac{D_t(i)\exp(\alpha_t(2I(y_i \neq h_t(x_i)) - 1))}{Z_t}$ (Eq. 2-4)

where $Z_t$ is a normalization factor.

Step E: Determination of Selected Bands.

For a two-class classification task, the selected spectral bands would be the first N bands with the largest weights computed in Step D, where N is a number set by the user. However, for a multi-class task, different sets of filters corresponding to different binary classification tasks would be selected, as the multi-class classification engine is typically broken down into a set of binary classification algorithms. The ensemble of the sets will eventually constitute more than N filters if sets of selected filters are not exactly the same.

In order to combine the N selected filters from the individual binary classification tasks, the weights calculated in Step D are combined to obtain a new set of weights W. Thus, in this example, the selected spectral bands from each task shown in Table B were combined. In combining the spectral bands, the weights corresponding to each spectral band and each binary task are combined to obtain a set of weights $W = \{W_\lambda, \lambda \in \{1, \ldots, 32\}\}$, where $W_\lambda$ is the combined weight for one spectral band. The combined weight is estimated as:

$$W_\lambda = \frac{1}{Z} \Sigma_i \exp\left(-\left(\frac{1 - \tilde{\alpha}_{i,\lambda}}{\tilde{\alpha}_{i,\lambda}}\right)^p\right),$$ (Equation 3-1)

where $\tilde{\alpha}_{i,\lambda}$ is the normalized weight of spectral band λ corresponding to the binary classification task i, Z is a normalization term which ensures that the sum of $W_\lambda$ over all spectral bands is one. The selected spectral bands are taken to be the first N bands with the largest $W_\lambda$'s. The shape of the mapping function in Equation (3-1) is determined by the parameter p. The mapping function maps the weights of spectral bands as estimated in the two-class classification tasks to the weights W. In this embodiment, p=0.5.

The technique described above is used to find the five (5) selected filters within a five-class classification framework. Table B, above, is repeated here for convenience. Table B shows the indexes of the first 5 filters with the largest weights for each pair of classes considered for the binary classification tasks within the five-class material classification framework. The last column shows the indexes of the filters selected for the five-class classification framework. These indexes are computed using the mapping function as described in Equation (3-1) of Step E above.

TABLE B (Repeated from above)

| | Task 1 | Task 2 | Task 3 | Task 4 | Task 5 | Task 6 | Task 7 | Task 8 | Task 9 | Task 10 | All |
|---|---|---|---|---|---|---|---|---|---|---|---|
| Index | 16 | 19 | 5 | 3 | 30 | 16 | 16 | 16 | 16 | 5 | 16 |
| of | 19 | 16 | 30 | 6 | 31 | 19 | 17 | 19 | 19 | 3 | 19 |

TABLE B-continued (Repeated from above)

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | All |
| selected | 17 | 18 | 10 | 5 | 14 | 11 | 18 | 9 | 14 | 4 | 5 |
| bands | 28 | 32 | 4 | 32 | 4 | 9 | 32 | 5 | 4 | 30 | 30 |
| | 29 | 21 | 31 | 4 | 18 | 18 | 21 | 3 | 18 | 31 | 3 |

The selection of spectral bands according to this Step E is depicted diagrammatically in FIG. 9. Referring again to FIG. 9, and as previously described, the filter selection algorithm depicted at 302 provides two outputs: weight determinations as depicted at 303, and selected spectral bands having the largest weights as depicted at 304. Selection of spectral bands proceeds according to this Step E of the framework. As described herein, there is a selection of N spectral bands having the largest weights of the 32 weights at 303. In the numerical example of FIG. 9, it will be observed that the three spectral bands corresponding to wavelengths λ2, λ18 and λ19 have the largest weights. As a result, these three spectral bands are included amongst the N=5 spectral bands selected in this embodiment. The selection of these spectral bands is highlighted by dashed lines which enclose these spectral bands at 304 in FIG. 9. Since in this example N=5, two other unshown spectral bands are also selected, so as to make up the complement of N=5 selected spectral bands with the largest weights.

<Part 2: Training and Classification Using Images Corresponding to the Selected Bands or Filters>

Given the labeled training samples and the N bands selected as described in the previous section (i.e., in Part 1), the classifiers can be trained and tested using the captured images corresponding to only the N bands. One goal of these experiments is to show that using images corresponding to only a subset N of the 32 spectral bands provides competitive performance in material classification. In this embodiment, N=5, i.e., a subset of 5 out of 32 spectral bands is selected. Different classification engines can be used and this embodiment uses the SVM with a linear kernel. The advantage of using an SVM is that it takes as input the features of different bands in one feature vector and therefore the information among spectral bands is taken into consideration.

The classifier is trained on multiple folds of training data and tested on the remaining folds. The total number of samples is split into 50% of training data and 50% of testing data. For each material category, there are four pieces of the material. Note that in this Part 2, the term "pieces" is used as compared with "samples" to distinguish between the samples as used in the classification algorithm. Since a sample is considered to be a pixel in the classification algorithm, the number of samples corresponding to one material category would be 4×M, where M is the number of pixels in an image of one piece of material. Given that there are two categories in a binary classification task, there would be 8×M samples in total. The samples are split into 6 folds of training and testing data. As mentioned earlier, half of the samples are taken to be training ones and the other half as testing ones. Also, it is assumed that there are equal numbers of samples from both categories in the test set and that the indices of the testing (or training) samples from both classes are the same. The classification accuracy computed is then taken to be the average over the classification accuracies of the test sets of the 6 folds.

Figure 12:
FIG. 12 shows seventeen (17) samples of 33 HDR (high dynamic range) images captured of Aluminum 2024 under one light source.

FIG. 12 illustrates 17 samples of the 33 HDR (high dynamic range) images captured of Aluminum 2024 under one light source.

In FIG. 12, the bands corresponding to the images shown have center wavelengths which were selected in the range of 400 nm to 720 nm with an increment of 20 nm.

Results obtained for these material classification experiments will now be presented.

Figure 13:
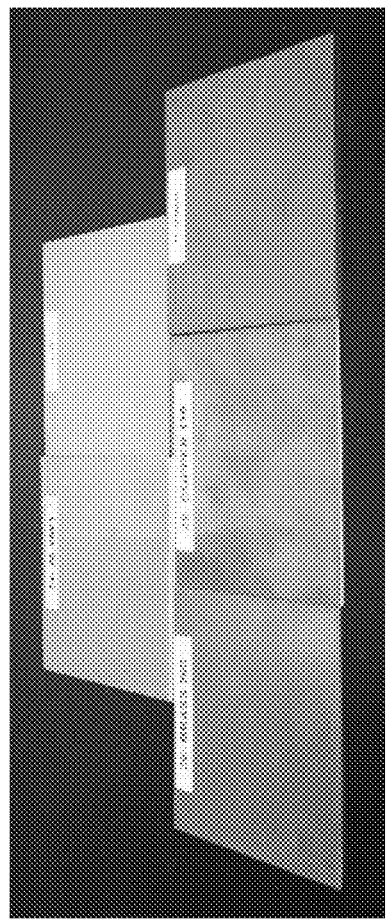
FIG. 13 shows a photograph of some of the samples of classified materials.

FIG. 13 shows a photograph of some of the samples of the materials classified in this experiment, namely, Aluminum, Tin, Brass, Copper, and Titanium.

To investigate the compromise on classification accuracy using images corresponding to a selected set of spectral bands as compared with all 32, five (5) material categories are taken from the database and classified using the images corresponding to the different numbers of filters. Results for classifying two different sets of five-(5) material categories are shown in Table C and Table D, respectively. The material categories for which results are shown in Table C are Nickel, Titanium, Tin, Aluminum, and Copper. The material categories for which results are shown in Table D are Zinc, Steel, Lead, Aluminum, and Brass. The tables show classification accuracies for each of the binary classification tasks within the five-class classification framework when images corresponding to 5 filters and 32 filters are used.

Table C thus shows classification accuracy for each binary classification task, for all ten (10) of the binary class pairs of the following five (5) materials: Nickel, Titanium, Tin, Aluminum, and Copper. In Table C, the top row shows classification accuracies using 5 selected spectral bands, whereas the bottom row shows classification accuracies using all 32 spectral bands. The indexes of the tasks are the same as the tasks in Table B, namely: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

TABLE C

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | Average |
| 5 bands | 99.99 | 99.99 | 70.62 | 98.83 | 97.10 | 99.98 | 99.99 | 99.98 | 99.99 | 99.75 | 96.63 |
| All bands | 99.99 | 100.0 | 77.35 | 99.62 | 94.82 | 100.0 | 100.0 | 100.0 | 100.0 | 99.88 | 97.17 |

Description of Table C: Classification accuracy for each binary classification task, comparing use of 5 selected spectral bands (top row) against use of all 32 spectral bands (bottom row) for a first set of five materials. The indexes of the tasks are: Task 1: Nickel vs. Titanium; Task 2: Nickel vs. Tin; Task 3: Nickel vs. Aluminum; Task 4: Nickel vs. Copper; Task 5: Titanium vs. Tin; Task 6: Titanium vs. Aluminum; Task 7: Titanium vs. Copper; Task 8: Tin vs. Aluminum; Task 9: Tin vs. Copper; and Task 10: Aluminum vs. Copper.

Likewise, Table D shows classification accuracy for each binary classification task, for all ten (10) of the binary class pairs of a different set of five (5) materials as compared against the five materials in Table C. In Table D, the materials are: Zinc, Steel, Lead, Aluminum and Brass. In Table D, the top row shows classification accuracies using 5 selected spectral bands, whereas the bottom row shows classification accuracies using all 32 spectral bands. The indexes of the tasks are: Task 1: Zinc vs. Steel; Task 2: Zinc vs. Lead; Task 3: Zinc vs. Aluminum; Task 4: Zinc vs. Brass; Task 5: Steel vs. Lead; Task 6: Steel vs. Aluminum; Task 7: Steel vs. Brass; Task 8: Lead vs. Aluminum; Task 9: Lead vs. Brass; Task 10: Aluminum vs. Brass.

TABLE D

| | Task number within the multi-class classification framework | | | | | | | | | | |
|---|---|---|---|---|---|---|---|---|---|---|---|
| | Task 1 | Task 2 | Task 3 | Task 4 | Task 5 | Task 6 | Task 7 | Task 8 | Task 9 | Task 10 | Average |
| 5 bands | 62.76 | 74.81 | 93.22 | 99.78 | 84.22 | 76.19 | 91.15 | 95.29 | 97.39 | 94.24 | 86.91 |
| All bands | 60.08 | 82.63 | 93.02 | 85.85 | 78.73 | 70.92 | 83.19 | 96.29 | 88.99 | 99.88 | 82.75 |

Description of Table D: Classification accuracy for each binary classification task, comparing use of 5 selected spectral bands (top row) against use of all 32 spectral bands (bottom row) for a second, different set of five materials. The indexes of the tasks are: Task 1: Zinc vs. Steel; Task 2: Zinc vs. Lead; Task 3: Zinc vs. Aluminum; Task 4: Zinc vs. Brass; Task 5: Steel vs. Lead; Task 6: Steel vs. Aluminum; Task 7: Steel vs. Brass; Task 8: Lead vs. Aluminum; Task 9: Lead vs. Brass; Task 10: Aluminum vs. Brass.

It can be seen that on average the 5-band results are comparable to the 32-band results, or that there is an improvement when using 5 bands. The improvement can be attributed to the fact that the most discriminative features corresponding to the selected bands are used in the classification engine in the 5-band case.

In order to more closely examine the impact of using different numbers of filters on the multi-class classification engine, different numbers of N selected filters were considered: 3, 5, 7, 11, 21, and 32. Table E and Table F list the classification accuracies for the multi-class classification framework when images corresponding to each of these numbers of filters are used. For Table E, the material categories used are Nickel, Titanium, Tin, Aluminum, and Copper (which are the same materials as those listed in Table C), and for Table F, the material categories used are Zinc, Steel, Lead, Aluminum and Brass (which are the same materials as those listed in Table D). As shown and as compatible with the results shown in Table C and Table D, increasing N does not necessarily lead to an increase in classification accuracy. Also, the compromise on classification accuracy is small even when images from a subset of filters or spectral bands from the 32 are used.

TABLE E

| 3 filters | 5 filters | 7 filters | 11 filters | 21 filters | 32 filters |
|---|---|---|---|---|---|
| 90.30 | 96.63 | 92.80 | 94.25 | 97.07 | 97.17 |

Description of Table E: The overall average classification accuracies for the multi-class classification engine when different numbers of filters are used. The materials are the same set of materials used for Table C, namely: Nickel, Titanium, Tin, Aluminum and Copper.

TABLE F

| 3 filters | 5 filters | 7 filters | 11 filters | 21 filters | 32 filters |
|---|---|---|---|---|---|
| 85.49 | 86.91 | 82.41 | 82.71 | 82.45 | 82.75 |

Description of Table F: The overall average classification accuracies for the multi-class classification engine when different numbers of filters are used. The materials are the same set of materials used for Table D, namely: Zinc, Steel, Lead, Aluminum and Brass.

Figure 10:
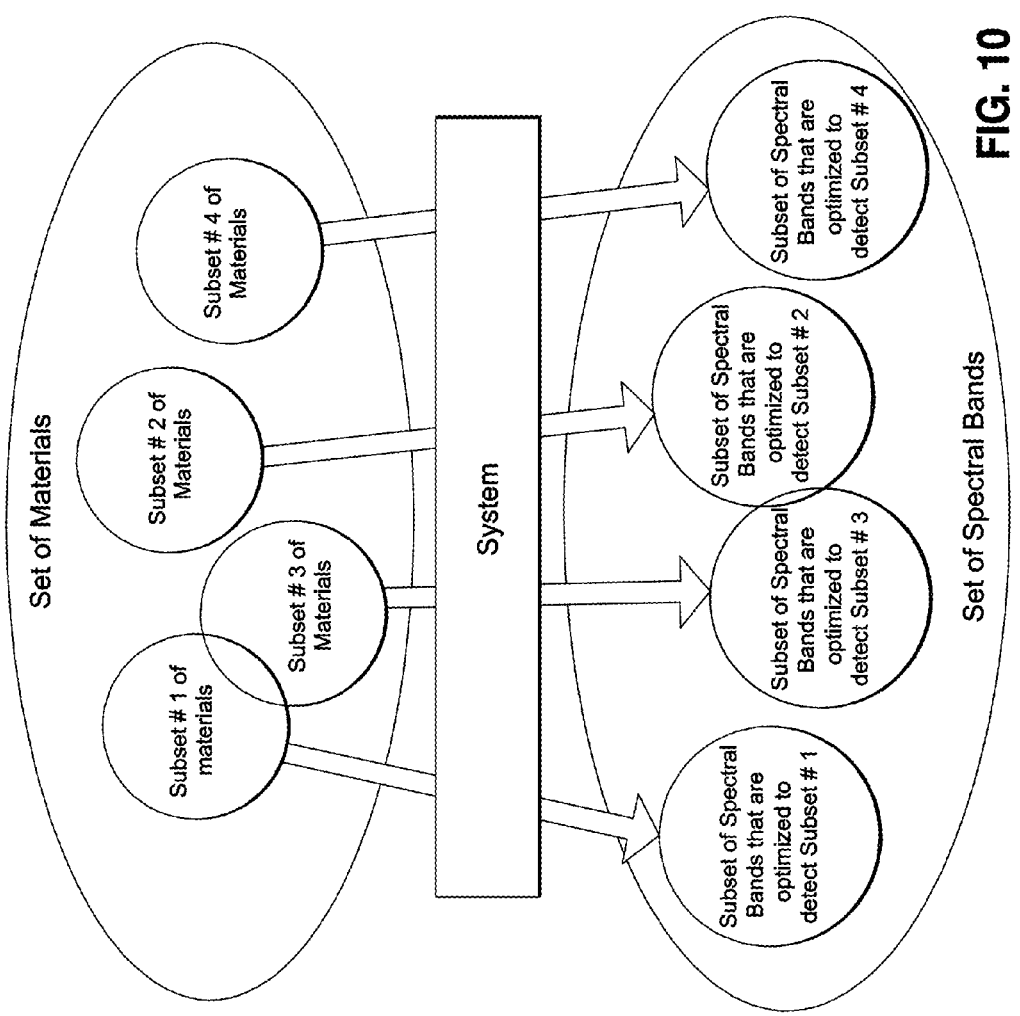
FIG. 10 illustrates some possible overlaps in subsets of materials in a given set of materials and some possible overlaps in subsets of spectral bands, each designed to differentiate between materials in respective ones of subsets of materials.

FIG. 10 illustrates some possible overlaps in subsets of materials in a given set of materials and some possible overlaps in subsets of spectral bands, each designed to differentiate between materials in respective ones of subsets of materials.

More specifically, as described hereinabove, a subset of spectral bands are selected that are optimized to classify the materials in a group of materials. The optimized subset of spectral bands allows classification of the materials in the group of materials without a significant loss of classification accuracy. Thus, if there is a set of materials, a set of spectral bands, and a first group, subset #1, of materials that are to be classified, the system determines the subset of spectral bands that are optimized to detect subset #1. Different optimized subsets of spectral bands may be generated for the different subsets of materials. For example, even though subset #1 and subset #3 overlap, their respective optimized subsets of spectral bands do not overlap. Also, although subset #2 and subset #3 do not overlap, their respective optimized subsets of spectral bands do overlap.

FIG. 10 illustrates some possibilities for this overlap. This figure illustrates some possible overlaps in subsets of materials in a given set of materials (such as Nickel, Titanium, Tin, Aluminum and Copper) and some possible overlaps in subsets of spectral bands, each designed to differentiate between materials in respective ones of the subsets of materials (such as a differentiation between each of the ten (10) combinations of two materials chosen from the five materials of Nickel, Titanium, Tin, Aluminum and Copper).

One advantage provided by the arrangements described herein is finding a small number of spectral bands (or equivalently filters), which can be used to image materials without compromising on material classification accuracy. The more filters in the image capture system, the longer it takes to image a material. Additionally, usage of images corresponding to additional filters does not necessarily increase the material classification accuracy as shown above.

Another advantage is the capability of reducing cost through replacing the LCTF of 32 bands by a filter wheel in which 5 selected filters can be used, such as for camera 24 in FIG. 1. The price of an LCTF for the visible wavelength range is in the order of $10,000, whereas the price for a broadband camera coupled with a simple filter wheel is much lower, thus allowing for deployment in multiple industrial inspection sites in the field.

In addition, knowing the five filters needed can allow for the design of a color filter array for material sensing. Such a filter would provide portability in robotics applications.

Other advantages which stem from the above are reducing the number of images captured and consequently the dimensionality of the feature vectors needed to represent the materials in the classification engine. For example, in a binary material classification case with one illumination setup, the capture time for one image would be 32 bands×5 sec=160 sec=2.67 minutes. Using only 5 bands, the capture time would be 5 bands×5 sec=25 sec. Additionally, the sizes of the feature vectors for the 32 band case and the 5 band case are about 100 Mb and 16 Mb respectively. This implies that the sizes of the feature vectors are reduced by a factor of 7 upon using a subset of filters. Note that in this example case, very few images are used, while in a factory or robotic industrial application setting, the number of images can scale considerably.

Reducing the sizes of the feature vectors would result in decreasing both the training and test time. Decreasing the training time would be useful in case of deployment of an online training material classifier. Decreasing the test time is important when a classifier is deployed in a factory setting for recycling.

As shown above, there has been described a technique for filter/spectral band selection using the captured images under multiplexed illumination. With such a technique, the number of filters can be reduced from 32 down to 3 or 4 or-5 while still achieving high classification accuracy. Some advantages include the replacement of the LCTF; and a reduction in capture time, image storage space, and classification time.

Other Embodiments

It will be appreciated that the features of the above embodiments can be combined one with the other in a manner that will be apparent to those of ordinary skill once informed by the description herein.

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a non-volatile memory card, a flash memory device, a storage of distributed computing systems and the like. The storage medium may be a function expansion unit removably inserted in and/or remotely accessed by the apparatus or system for use with the computer processor(s).

This disclosure has been presented for purposes of illustration and description but is not intended to be exhaustive or limiting. Many modifications and variations will be apparent to those of ordinary skill in the art who read and understand this disclosure, and this disclosure is intended to cover any and all adaptations or variations of various embodiments. The example embodiments were chosen and described in order to explain principles and practical application, and to enable others of ordinary skill in the art to understand the nature of the various embodiments. Various modifications as are suited to particular uses are contemplated. Suitable embodiments include all modifications and equivalents of the subject matter described herein, as well as any combination of features or elements of the above-described embodiments, unless otherwise indicated herein or otherwise contraindicated by context or technological compatibility or feasibility.

The invention claimed is:

1. A method for selecting spectral bands for material classification in which material classification uses multi-spectral BRDF (bidirectional reflectance distribution function) slice images captured under multiplexed illumination, the method comprising: analysis of a database of labeled training material samples within a multi-class classification framework, captured using a large number of spectral bands, so as to select a subset of spectral bands, wherein the number of selected spectral bands in the subset is smaller than the large number of spectral bands, wherein the selected spectral bands in the subset have a significant aptitude for distinguishing between different classifications of materials, and wherein the significant aptitude for distinguishing between different classifications of materials comprises an aptitude such that accuracy of material classification using the selected spectral bands in the subset are comparable to accuracy of material classification using the large number of spectral bands.

2. The method of claim 1, wherein analysis comprises:
accessing a database of labeled training material samples within a multi-class classification framework, the samples being captured using a relatively large number of spectral bands;
computing feature vector representations of these materials;
learning a set of weights representing the importance of the spectral bands on the features in each binary classification task;
converting the weights from the binary classification tasks to a set of weights for the multi-class classification framework using a mapping function; and
selecting spectral bands of highest weight as the selected spectral bands.

3. The method of claim 2, wherein learning a set of weights representing the importance of the spectral bands comprises application of an Adaboost algorithm.

4. The method of claim 2, further comprising training of a classification engine using the selected spectral bands, the corresponding images obtained using them, and feature vector representations computed from the material samples using these images.

5. The method of claim 2, wherein the feature vectors are pixel intensities of spectral BRDF (bidirectional reflectance distribution function) slice images captured under multiplexed illumination.

6. The method of claim 2, wherein the feature vector representations are learned using pixel intensities of spectral BRDF (bidirectional reflectance distribution function) slice images captured under multiplexed illumination.

7. The method of claim 2, wherein the training images are labeled by material by calculating a probability function based on determining a correlation between a sample signature and a set of pre-labeled signatures in a database.

8. The method of claim 2, wherein the number of selected spectral bands is selected automatically, using thresholding on the weights.

9. The method of claim 2, wherein material sub-categories are considered.

10. The method according to claim 1, wherein the accuracy of material classification using the selected spectral bands in the subset and the accuracy of material classification using the large number of spectral bands are within around 6.87% of each other.

11. The method according to claim 1, wherein there are around 32 or more spectral bands in the large number of spectral bands, and the number of selected spectral bands is between 5 and 11.

12. A method for material classification of an object fabricated from an unknown material, comprising:
illuminating an object by multiplexed illumination;
measuring multiple spectral bands of light reflected from the illuminated object; and
classifying the material from which the object is fabricated using the measured reflected light;
wherein with respect to the measured multiple spectral bands, wavelengths for the multiple spectral bands are selected by analysis of a database of labeled training material samples within a multi-class classification framework, captured using a large number of spectral bands, so as to select a subset of spectral bands, wherein the number of selected spectral bands in the subset is smaller than the large number of spectral bands, wherein the selected spectral bands in the subset have a significant aptitude for distinguishing between different classifications of materials in the database, and wherein the significant aptitude for distinguishing between different classifications of materials in the database comprises an aptitude such that accuracy of material classification using the selected spectral bands in the subset are comparable to accuracy of material classification using the large number of spectral bands.

13. The method of claim 12, wherein the multiple spectral bands are selected by steps which include:
computing feature vector representations of the materials in the database;
learning a set of weights representing the importance of the spectral bands on the features in each binary classification task;
converting the weights from the binary classification tasks to a set of weights for the multi-class classification framework using a mapping function; and
selecting spectral bands of highest weight as the selected spectral bands.

14. The method of claim 13, wherein learning a set of weights representing the importance of the spectral bands comprises application of an Adaboost algorithm.

15. The method of claim 1, further comprising computing feature vector representations from the measured spectral bands.

16. The method of claim 15, wherein the feature vectors are pixel intensities of spectral BRDF (bidirectional reflectance distribution function) slice images captured under multiplexed illumination.

17. The method of claim 15, wherein the feature vector representations are learned using pixel intensities of spectral BRDF (bidirectional reflectance distribution function) slice images captured under multiplexed illumination.

18. The method of claim 1, wherein classification comprises applying a trained classification engine to the captured light information to classify the material of the illuminated object.

19. The method of claim 18, wherein material sub-categories are considered.

20. The method of claim 18, wherein the trained classification engine makes a decision for cases with a pre-determined level of confidence in the prediction.

21. The method of claim 20, wherein responsive to a decision not being made, the sample is subjected to manual labeling.

22. The method of claim 18, wherein the trained classification engine is trained on-line with new material samples.

23. The method of claim 18, wherein the trained classification engine makes a decision for cases with a pre-determined level of confidence in the prediction, wherein responsive to a decision not being made, the sample is subjected to manual labeling in which the sample is placed into an online material classifier.

24. The method of claim 1, wherein the accuracy of material classification using the selected spectral bands in the subset and the accuracy of material classification using the large number of spectral bands are within around 6.87% of each other.

25. The method of claim 1, wherein there are around 32 or more spectral bands in the large number of spectral bands, and the number of selected spectral bands is between 5 and 11.

26. An apparatus for material classification of an object fabricated from an unknown material, comprising:
  memory for storing computer-executable process steps and for storing labeled training data; and
  one or more processors for executing the computer-executable process step stored in the memory;
  wherein the computer-executable process steps include steps to:
  illuminate an object by multiplexed illumination;
  measure multiple spectral bands of light reflected from the illuminated object; and
  classify the material from which the object is fabricated using the measured reflected light;
  wherein with respect to the measured multiple spectral bands, wavelengths for the multiple spectral bands are selected by analysis of a database of labeled training material samples within a multi-class classification framework, captured using a large number of spectral bands, so as to select a subset of spectral bands, wherein the number of selected spectral bands in the subset is smaller than the large number of spectral bands, wherein the selected spectral bands in the subset have a significant aptitude for distinguishing between different classifications of materials in the database, and wherein the significant aptitude for distinguishing between different classifications of materials in the database comprises an aptitude such that accuracy of material classification using the selected spectral bands in the subset are comparable to accuracy of material classification using the large number of spectral bands.

27. The apparatus according to claim 26, wherein the accuracy of material classification using the selected spectral bands in the subset and the accuracy of material classification using the large number of spectral bands are within around 6.87% of each other.

28. The apparatus according to claim 26, wherein there are around 32 or more spectral bands in the large number of spectral bands, and the number of selected spectral bands is between 5 and 11.

29. An apparatus for selecting spectral bands for material classification in which material classification uses multi-spectral BRDF (bidirectional reflectance distribution function) slice images captured under multiplexed illumination, comprising:
  memory for storing computer-executable process steps and for storing labeled training data; and
  one or more processors for executing the computer-executable process step stored in the memory;
  wherein the computer-executable process steps include steps wherein the spectral bands are selected by analysis of a database of labeled training material samples within a multi-class classification framework, captured using a large number of spectral bands, so as to select a subset of spectral bands, wherein the number of selected spectral bands in the subset is smaller than the large number of spectral bands, wherein the selected spectral bands in the subset have a significant aptitude for distinguishing between different classifications of materials, and wherein the significant aptitude for distinguishing between different classifications of materials comprises an aptitude such that accuracy of material classification using the selected spectral bands in the subset are comparable to accuracy of material classification using the large number of spectral bands.

30. The apparatus according to claim 29, wherein the accuracy of material classification using the selected spectral bands in the subset and the accuracy of material classification using the large number of spectral bands are within around 6.87% of each other.

31. The apparatus according to claim 29, wherein there are around 32 or more spectral bands in the large number of spectral bands, and the number of selected spectral bands is between 5 and 11.

* * * * *